United States Patent
Wang et al.

(10) Patent No.: US 9,687,433 B2
(45) Date of Patent: Jun. 27, 2017

(54) ANHYDROUS DEPIGMENTING COMPOSITIONS COMPRISING PHENOLIC COMPOUNDS

(71) Applicant: Ecstasy LLC, Chapel Hill, NC (US)

(72) Inventors: Xiaodong Wang, Chapel Hill, NC (US); Hua Zhong, Basking Ridge, NJ (US)

(73) Assignee: Ecstasy LLC, Chapel Hill, NC (US)

( * ) Notice: Subject to any disclaimer, the term of this patent is extended or adjusted under 35 U.S.C. 154(b) by 0 days.

(21) Appl. No.: 14/879,704

(22) Filed: Oct. 9, 2015

(65) Prior Publication Data

US 2017/0100318 A1    Apr. 13, 2017

(51) Int. Cl.
 *A61Q 19/02* (2006.01)
 *A61K 8/49* (2006.01)
 *C07D 309/12* (2006.01)

(52) U.S. Cl.
 CPC .............. *A61K 8/498* (2013.01); *A61Q 19/02* (2013.01); *C07D 309/12* (2013.01)

(58) Field of Classification Search
 CPC ....... A61K 8/498; C07D 309/12; A61Q 19/02
 USPC ............................................ 424/62, 401, 49
 See application file for complete search history.

(56) References Cited

U.S. PATENT DOCUMENTS

| | | | |
|---|---|---|---|
| 8,758,785 B2 | 6/2014 | Miyamoto et al. | |
| 2003/0232091 A1* | 12/2003 | Shefer | A61K 8/671 424/490 |
| 2013/0224137 A1 | 8/2013 | Kvalnes et al. | |
| 2013/0243710 A1* | 9/2013 | Koganov | A61K 8/97 424/62 |

OTHER PUBLICATIONS

Boissy et al. "DeoxyArbutin: a novel reversible tyrosinase inhibitor with effective in vivo skin lightening potency", *Experimental Dermatology* 14:601-608 (2005).
Notification of Transmittal of the International Search Report and the Written Opinion of the International Searching Authority, or the Declaration corresponding to International Application No. PCT/US2015/054883 mailed May 12, 2016.

* cited by examiner

*Primary Examiner* — Yanzhi Zhang
(74) *Attorney, Agent, or Firm* — Myers Bigel, P.A.

(57) ABSTRACT

The present invention is relates to a novel anhydrous dermatological depigmenting compositions comprising a phenolic compound, and methods of making and using the same.

27 Claims, No Drawings

ANHYDROUS DEPIGMENTING COMPOSITIONS COMPRISING PHENOLIC COMPOUNDS

BACKGROUND OF THE INVENTION

Technical Field

The present invention relates to novel highly stable topically applicable cosmetic and/or dermatological compositions comprising depigmenting agents for treating the skin of the face and/or body for the purposes of lightening the skin, evening skin tone and/or treating areas of hyperpigmentation.

Background of Related Art

Consumers of skin lightening products spend more than $1 billion annually in search of skin with an even tone on their faces, hands and bodies. The development of areas of hyperpigmentation on the skin is obviously of great concern to these individuals. The hyperpigmented areas are caused by a concentration of melanin in the keratinocytes located at or near the skin surface. Melanin pigment is produced in melanocytes in highly specialized organelles known as melanosomes. Melanocytes are found in several locations throughout the body, including in the bottom layer of the skin's epidermis, the iris of the eye and the hair. Manufacturing of melanin begins when melanin-making enzymes are activated and transform the amino acid tyrosine to intermediates of the end product, melanin. The actual production of melanin begins in the melanosomes. Inside human melanosomes, a series of chemical reactions, catalyzed by enzymes, converts tyrosine into two types of melanin, eumelanin, which is brown or black in color, and pheomelanin, which is red or yellow.

Humans possess a variety of skin colors distributed among of races around the world. Epidermal coloration in humans is controlled by melanocytes, located in the base portion of the epidermis, where a complicated combination of cellular procedures is conducted (Raper, H. S., "The Anaerobic Oxidases," *Physiol. Rev.* 1928, 8, 245-282; Mason, H. S., "The Chemistry of Melanin. III. Mechanism of the Oxidation of Trihydroxyphenylalanine by Tyrosinase, *J. Biol. Chem.* 1948, 172, 83-99; Cooksey, et al., "Evidence of the Indirect Formation of the Catecholic Intermediate Substrate Responsible for the Autoactivation Kinetics of Tyrosinase," *J. Biol. Chem.* 1997, 272, 26226-26235; Chang T. S., "An Updated Tyrosinase Inhibitors," *Int. J. Mol. Sci.* 2009, 10, 2440-2475). These processes, in addition to the catalytic reaction of tyrosinase, the major critical and rate-controlling step, result in the synthesis and transfer of a pigment, melanin. Melanin, which besides being responsible for skin color and tone, is the key physiological defense factor against sun injury, such as sunburn, photoaging and photocarcinogenesis. Therefore, tyrosinase is a recognized molecular target of discovery and development of hypopigmenting agents for medical dermal pigment conditions (disorders) and cosmetics (Chang T. S., "An Updated Tyrosinase Inhibitors," *Int. J. Mol. Sci.* 2009, 10, 2440-2475).

Hyperpigmentation, hypopigmentation, and other pigmentation disorders are quite common and can be caused by a verity of factors, including genetics, living and daily working environment, some medical conditions, medications, excessive sun exposure, etc. Common pigmentation disorders include melasma (dark patches appearing during or after pregnancy) and liver spots (which often develop with age), and may arise as a side effect of birth control pills, and/or as a persistent result of acne, burns, bites and other skin injuries. Similarly, freckles, chloasma and pigmentary deposits after sun exposure tend to occur or increase or become difficult to lighten with increasing age, thus being one of the more disconcerting and/or common problems of skin care for persons of middle to advanced age. Post inflammatory hyper-pigmentation might occur following any inflammatory state of the skin such as chemical burns or following laser therapy. In order to obtain brighter/lighter skin or address pigmentation disorders effectively and simply, many compositions have been formulated. The use of such compositions is not limited to treating medical pigmentation disorders, but also in some cultures/markets merely for the purpose of changing or whitening ones natural healthy skin for cosmetic purpose.

A large number of agents and methods for skin depigmentation or hypopigmentation have been discovered, developed and used on cosmetic market. The most commonly and effectively employed hypopigmentation agent is hydroquinone (HQ). However, while effective, HQ has serious adverse side effect (D. C. Topping, et al., *Food and Chemical Toxicology*, 45 (2007) 70-78; J. C. English, et al., *Fundam. Appl. Toxicol.* 23 (1994) 391-396; J. C. English, et al., *Fundam. Appl. Toxicol.* 23 (1994) 397-406; R. Charlin, et al., *International Journal of Dermatology*, 2008, 47, 19-23; Y. M. Olumide, et al., *International Journal of Dermatology*, 2008, 47, 344-353; T. W. Tse, *Journal of Dermatological Treatment* 2010, 21, 272-275; R. J. Bqatman, et al., *Journal of Toxicology and Environmental Health*, 1996, 47:2, 159-172; R. Barale, et al., *Mutation Research*, 244 (1990) 15-20; M. L. Robertson, et al., *Mutation Research*, 249 (1991) 201-209; Q. Li, et al., *Toxicol. Appl. Pharmacol.* 1996, 139, 317-323; G. C. Jagetia, et al., *Toxicology Letters*, 93 (1997) 205-213; V. V. Subrahmanyam, et al., *Toxicology*, 62 (1990) 107-116), even though the cancer causal association was not clearly determined (D. E. Rollison, et al., *Journal of Toxicology and Environmental Health*, Part B, 2006, 9:413-439). In many parts of the world, including the European Union and China, hydroquinone is banned for cosmetic product. The Chinese FDA regulation for hydroquinone use is that the highest allowed concentration for hydroquinone in any cosmetic products is 0.002% (20 ppm). Although to date sales of cosmetic products containing hydroquinone are allowed in the United States, safety concerns have also been expressed by the US FDA. There remains a need for stable formulations for a safer alternative to hydroquinone.

The activity and potency of deoxyarbutin (4-[(tetrahydro-2H-pyran-2-yl) oxy] phenol) tyrosinase inhibitors is well-known and well-documented in the literature. See, for example: Hamed, et al., *J. Cosmet. Sci.* 54(4) 2006 291-308; and Boissy, et al., *Experimental Dermatology* 14(8) 2005, 601-608. It is safer and less irritating than hydroquinone, However, all attempts to create a stable, non-browning topical formulation have been unsuccessful. It has been shown that deoxyarbutin is a thermolabile and acid sensitive compound in aqueous solutions and degraded to hydroquinone (Chao-Hsun Yang, et al., *Int. J. Mol. Sci.* 2010, 11, 3977-3987). It is known for its great sensitivity to hydrolysis, to oxidation and to heat, leading to generation of hydroquinone. U.S. Patent Application Pub. No. US2013/0224137, which describes a composition comprising deoxyarbutin. In this case, the hydroquinone is generated in significant amount over time. The commercial products, such as Prevage MD (Allergan) that contained deoxyarbutin, were withdrawn from the market, in part because the creams quickly became colored. An attempt to create a stable anhydrous topical formulation also failed (Chih-Chien Lin, et al., *Int. J. Mol. Sci.* 2011, 12, 5946-5954). The results of this study indicated that water increased the decomposition of deoxyarbutin in the formulations, and that a polyol-in-silicone, oil-based, anhydrous emulsion system provided a relatively stable surrounding for the deoxyarbutin that delayed its degradation at 25° C. and 45° C. However, generation of hydroquinone is still observed in relatively significant amount.

A formulation of a depigmenting agent, e.g., deoxyarbutin, in which the vehicle retarded oxidation and decomposition of depigmenting agent (e.g., retarded oxidation and decomposition of deoxyarbutin to hydroquinone) and was appropriate and acceptable for topical application, particularly to the face, would represent a significant improvement in the art.

SUMMARY OF THE INVENTION

The present invention provides a solution to many of the problems previously identified with topical depigmenting formulations. Described herein are anhydrous physically and chemically stable formulations of skin lightening or depigmenting agents that resist browning and remain stable on storage at room temperature for extended periods. In various embodiments, the formulations of the invention remain stable even when exposed at higher temperatures, for months rather than hours. In particular, exemplary formulations of the invention resist oxidation and decomposition of the depigmenting agent in the formulation.

In various embodiments, the present invention provides a cosmetic or pharmaceutical dermatological formulation of use in depigmenting skin or otherwise lightening the tone of skin to which it is applied. In an exemplary embodiment, the active depigmenting ingredient has a structure according to Formula (I):

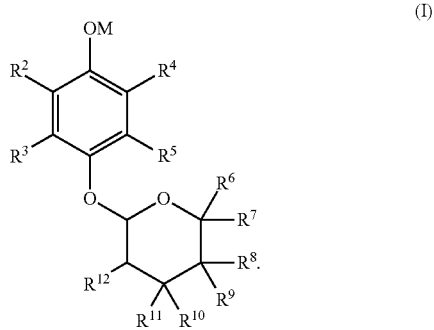

In Formula (I) $R^1$, $R^2$, $R^3$, $R^4$, $R^5$, $R^6$, $R^7$, $R^8$, $R^9$, $R^{10}$, $R^{11}$, and $R^{12}$ are independently selected from H, substituted or unsubstituted alkyl, substituted or unsubstituted heteroalkyl, substituted or unsubstituted aryl, substituted or unsubstituted heteroaryl, halogen, CN, $CF_3$, acyl, $-SO_2NR^{13}R^{14}$, $-NR^{13}R^{14}$, $-S(O)_2R^{13}$, $-C(O)R^{13}$, $-COOR^{13}$, $-CONR^{13}R^{14}$, $-S(O)_2OR^{13}$, $-OC(O)R^{13}$, $-C(O)NR^{13}R^{14}$, $-NR^{13}C(O)R^{14}$, $-NR^{13}SO_2R^{14}$, $NR^{13}C(O)NR^{14}R^{15}$, $C(NR^{13})R^{10}$, and $-NO_2$, wherein two or more of $R^1$, $R^2$, $R^3$, $R^4$, $R^5$, $R^6$, $R^7$, $R^8$, $R^9$, $R^{10}$, $R^{11}$, and $R^{12}$, together with the atoms to which they are bonded, are optionally joined to form a ring system which is a member selected from substituted or unsubstituted cycloalkyl, substituted or unsubstituted heterocycloalkyl, substituted or unsubstituted aryl and substituted or unsubstituted heteroaryl.

In various embodiments, $R^{13}$, $R^{14}$, and $R^{15}$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, and two or more of $R^{13}$, $R^{14}$, and $R^{15}$, together with the atoms to which they are bonded, are optionally joined to form a 5- to 7-membered ring which is a member selected from substituted or unsubstituted cycloalkyl, substituted or unsubstituted heterocycloalkyl, substituted or unsubstituted aryl and substituted or unsubstituted heteroaryl.

M is H or a counterion component of a salt of a phenol. Exemplary counterions are those found in dermatologically acceptable salts as this term is discussed herein.

In an exemplary embodiment, the active agent according to Formula (I) is deoxyarbutin. In an exemplary embodiment, the active agent is deoxyarbutin and the formulation is essentially free of hydroquinone, either added or produced by degradation of the deoxyarbutin to hydroquinone.

In various embodiments, the formulation is essentially anhydrous.

The active agent according to Formula (I) is present in formulations of the invention as a micronized small particle or dissolved in an alcohol vehicle. The micronized active agent or a solution of the active agent in an alcohol vehicle according to Formula (I) is incorporated into a dermatologically acceptable anhydrous carrier, such as a gel, paste, cream, etc.

Also provided by the present invention are methods of utilizing the formulations of the invention to alter skin pigmentation. In an exemplary embodiment, the method includes the topical application of an effective amount of a composition of the invention. In various embodiments, the topical application is repeated a sufficient number of applications for a duration of treatment to provide a change in skin pigmentation.

Other embodiments, objects and advantages of the invention are apparent from the detailed description that follows.

DETAILED DESCRIPTION OF THE INVENTION

Introduction

One aim of the present invention is to incorporate small particle or micronized active agent according to Formula (I) into a topical dermatologic formulation. Another aim of the present invention is to dissolve a phenolic active agent, e.g., the active agent according to Formula (I), in an anhydrous alcoholic solvent in which the active agent is both soluble and stable over a selected period of time. This solution is then incorporated into a manufacturing process for a topical dermatologic formulation. Another aim of the present invention is to provide an anhydrous pharmaceutical and cosmetic composition for topical application having prolonged stability without significant formation of hydroquinone, allowing optimized release of the active agent while at the same time being very well tolerated by the subject to whom it is administered. The present invention thus provides a novel anhydrous stable composition, especially for topical application, comprising a phenolic derivative.

In an exemplary embodiment, the present invention provides an anhydrous pharmaceutical composition comprising a pharmaceutical active agent of Formula (I). In exemplary formulations, the phenolic derivative is micronized to a small particle and suspended in a fatty phase of the formulation of the invention. In exemplary formulations, the composition comprises an oily phase that is a solvent for the active agent of Formula (I) and a fatty phase that is a non-solvent for the active agent. In various formulations, the active is in the form of particles suspected in the oily mixture. In various formulations, the active is dissolved in an oil phase (e.g., an organic solvent, e.g., an alcohol, or a mixture including an organic solvent), which is combined with a fatty phase.

DEFINITIONS

All percentages and ratios used herein are by weight of the total composition and all measurements made are at 25° C., unless otherwise designated. All numeric ranges are inclusive of narrower ranges; delineated upper and lower range limits are interchangeable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

"Phenolic active agent" and "active agent" are used interchangeably and, as these terms are used herein, refer to phenol agents that have activity in reducing or otherwise altering skin pigmentation. By way of example, mention can be made in a non-limiting manner of polyphenols and more particularly (4-tetrahydro-pyran-2-yloxy)-phenol and (4-tetrahydro-pyran-2-yloxy)-phenol salts thereof, is preferably used. The term "(4-tetrahydro-pyran-2-yloxy)-phenol salts" especially means salts formed with a dermatologically acceptable base, e.g., a mineral base such as sodium methoxide, sodium hydroxide, potassium tert-butoxide.

In exemplary formulations, the amount of phenolic derivative is from 0.01% to 20% by weight, preferably from about 0.05% to about 6% by weight and more particularly from 0.1% to 6% by weight relative to the total weight of the composition.

In exemplary formulations, the form of the phenolic derivative is either a solid or it is dissolved in an oily phase of the invention (e.g., an anhydrous alcoholic solvent), which is itself dispersed in, suspended in or dissolved in a fatty phase of the formulation.

As used herein, the term "oily phase" refers to a phase in which the active agent is dissolved. An oily phase may include one or more organic solvent in which the active is soluble. An exemplary organic solvent of the oily phase is an alcohol, a diol, or alcohols with multiple hydroxyl groups e.g., an anhydrous alcohol. Alcohols of use in dermatological preparations are known to those of skill in the art and include, without limitation, methanol, ethanol, and straight- and branched-propanol and butanol.

As used herein, the term "fatty phase" refers to a phase in which the active is not substantially soluble. Exemplary components of the fatty phase include those components that impart to gels, salves, pastes and ointments their characteristic flow, appearance and skin feel.

In exemplary formulations, the form of phenolic derivative is a solid with particle sizes ranged from about 0.01 micrometer (μm) to about 1,000 micrometer (μm) in diameter, e.g., from about 0.1 μm to about 100 μm in diameter, e.g., from about 0.2 μm to about 50 μm in diameter.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$CO_2R'$— represents both —C(O)OR' and —OC(O)R'.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "fluoroalkyl," are meant to include monofluoroalkyl and polyfluoroalkyl.

The term "aryl," employed alone or in combination with other terms (e.g., aryloxy, arylthioxy, arylalkyl), means, unless otherwise stated, an aromatic substituent which can be a single ring or multiple rings (up to three rings), which are fused together or linked covalently. "Heteroaryl" are those aryl groups having at least one heteroatom ring member. Typically, the rings each contain from zero to four heteroatoms selected from N, O, and S, wherein the nitrogen and sulfur atoms are optionally oxidized, and the nitrogen atom(s) are optionally quaternized. The "heteroaryl" groups can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl ring systems are selected from the group of acceptable substituents described below. The term "arylalkyl" is meant to include those radicals in which an aryl group is attached to an alkyl group (e.g., benzyl, phenethyl, pyridylmethyl and the like) or a heteroalkyl group (e.g., phenoxymethyl, 2-pyridyloxymethyl, 3-(1-naphthyloxy)propyl, and the like).

Each of the above terms (e.g., "alkyl," "heteroalkyl" and "aryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: substituted or unsubstituted alkyl, substituted or unsubstituted heteroalkyl, substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2 m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: substituted or unsubstituted alkyl, substituted or unsubstituted heteroalkyl, substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR", —NR—C(NR'R")=NR'", —S(Q)R', —S(O)$_2$R', —S(O)$_2$NR'R", —NRSO$_2$R', —CN and —NO$_2$, —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present.

Two of the substituents on adjacent atoms of the aryl ring may optionally be replaced with a substituent of the formula -T-C(O)-(CH$_2$)$_q$—U—, wherein T and U are independently —NH—, —O—, —CH$_2$— or a single bond, and the subscript q is an integer of from 0 to 2. Alternatively, two of the substituents on adjacent atoms of the aryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C$_1$-C$_6$)alkyl.

The term "dermatologically acceptable salts" includes salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of dermatologically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of dermatologically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., *Journal of Pharmaceutical Science*, 66: 1-19 (1977)). Certain specific compounds of the present invention contain both basic and acidic functionalities that allow the compounds to be converted into either base or acid addition salts.

As set out above, certain active agents according to Formula (I) may contain a basic functional group, such as amino or alkylamino, and are, thus, capable of forming dermatologically acceptable salts with pharmaceutically acceptable acids. The term "dermatologically acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, sulfamate, bisulfate, phosphate, nitrate, acetate, valerate, oleate, palmitate, stearate, laurate, benzoate, lactate, tosylate, citrate, maleate, ascorbate, palmitate, fumarate, succinate, tartrate, napthylate, mesylate, hydroxymaleate, phenylacetate, glutamate, glucoheptonate, salicyclate, sulfanilate, 2-acetoxybenzoate, methanesulfonate, ethane disulfonate, oxalate, isothionate, lactobionate, and laurylsulphonate salts and the like. See, for example, Berge et al. (1977) "Pharmaceutical Salts", *J. Pharm. Sci.* 66:1-19.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain active agents of use in the formulations of the present invention can exist in unsolvated forms as well as solvated forms, however, it is generally preferred that they not be in a hydrated form. In general, the solvated forms are equivalent to unsolvated forms and are encompassed within the scope of the present invention. Certain compounds of use in the present invention may exist in multiple crystalline or amorphous forms. In general, all physical forms are equivalent for the uses contemplated by the present invention and are intended to be within the scope of the present invention. "Compound or a dermatologically acceptable salt or solvate of a compound" intends the inclusive meaning of "or", in that a material that is both a salt and a solvate is encompassed.

Certain compounds of use in the present invention possess asymmetric carbon atoms (optical centers) or double bonds; the racemates, diastereomers, geometric isomers and individual isomers are encompassed within the scope of the present invention. Optically active (R)- and (S)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

The graphic representations of racemic, ambiscalemic and scalemic or enantiomerically pure compounds used herein are taken from Maehr, *J. Chem. Ed.*, 62: 114-120 (1985): solid and broken wedges are used to denote the absolute configuration of a chiral element; wavy lines indicate disavowal of any stereochemical implication which the bond it represents could generate; solid and broken bold lines are geometric descriptors indicating the relative configuration shown but not implying any absolute stereochemistry; and wedge outlines and dotted or broken lines denote enantiomerically pure compounds of indeterminate absolute configuration.

The compounds of use in the present invention may also contain unnatural proportions of atomic isotopes at one or more of the atoms that constitute such compounds. For example, the compounds may be labeled with isotopes, such as for example deuterium ($^2$H), tritium ($^3$H), iodine-125 ($^{125}$I), or carbon-13 ($^{13}$C) or carbon-14 ($^{14}$C). All isotopic variations of the compounds of the present invention, whether radioactive or not, are intended to be encompassed within the scope of the present invention.

The term "apply" or "application" as used in reference to a composition, means to apply or spread the dermatologic formulations of the present invention onto a mammalian skin surface such as the epidermis.

The term "dermatologically acceptable" as used herein means that the compositions or components described are suitable for use in contact with human skin tissue without undue toxicity, incompatibility, instability, allergic response, and the like.

The term "effective amount" as used herein means an amount of a compound or composition sufficient to significantly induce a positive benefit, e.g., lightening of pigmentation.

The term "post-inflammatory hypopigmentation" as used herein refers to an acute to chronic decrease in pigmentation as a response to a transient inflammatory event.

The term "hypopigmented spot" as used herein refers to a defined area of skin wherein the pigmentation is less than that of an adjacent area of skin due to localized and chronic or systemic underproduction of melanin.

The term "skin tone agent" as used herein refers to a composition of the invention that regulates melanin production signals, synthesis of melanin, systemic transfer of melanin between the melanocyte and the keratinocyte, and/or melanin degradation. Skin tone agents can improve the appearance of uneven skin tone by acting as a pigmentation enhancing cosmetic agent.

The term "skin tone" as used herein refers to the overall appearance of melanin in the skin caused by the systemic, rather than transient, synthesis of melanin. Skin tone is typically characterized over a larger area of the skin. The area ideally may be than 100 $mm^2$, but larger areas are envisioned such as the entirety of the facial skin or any of the facial skin surfaces. Skin tone can be measured by image analysis. For example, overall lightness can be measured by L* coordinate in L*a*b* color space (International Commission on Illumination). Chromophore mapping such as melanin mapping and melanin concentration may be used as an indicator of overall skin tone. Mean melanin may be calculated from the chromophore map data. Additionally, skin tone evenness can be determined by melanin evenness which also may be calculated from the chromophore map data. Suitable chromophore mapping techniques are discussed in the example below.

The term "facial skin surface" as used herein refers to one or more of forehead, periorbital, cheek, perioral, chin, and nose skin surfaces.

The term "anhydrous composition" or "anhydrous formulation" are used interchangeably and they refer to a composition comprising an amount of water of less than about 5%, less than about 4%, less than about 3%, less than about 2%, less than about 1% or less than about 0.5% by weight relative to the total weight of the composition. In various embodiments, the formulation is a multicomponent mixture and each component adds no more than about 0.01% water by weight relative to the total weight of the composition.

In an exemplary embodiment, the definition of "anhydrous composition" is operative. In this definition, the composition contains water in an amount that does not lead to water-mediated formation of a degradation product of the active agent according to Formula I. In an exemplary embodiment, the degradation product is a quinone, e.g., hydroquinone.

In one preferred mode according to the invention, the anhydrous composition does not contain sufficient water to be detectable by Karl Fischer titration or Karl Fischer techniques.

The term "stable composition" means a chemically and physically stable composition.

The term "chemical stability" especially means that no degradation of the active agent is observed over time and at temperatures from about 4 to about 40° C. An exemplary degradation product is hydroquinone. In an exemplary embodiment, the active agent according to Formula I is deoxyarbutin and this agent is not significantly converted to hydroquinone during storage. In an exemplary embodiment, not more than about 1 ppm, not more than about 5 ppm, not more than about 10 ppm, not more than about 15 ppm, not more than about 20 ppm, not more than about 25 ppm, not more than about 50 ppm, not more than about 100 ppm or not more than about 200 ppm of the active agent undergoes degradation while the formulation is stored at 25° C. for at least about 30 days, at least about 45 days, at least about 60 days, at least about 90 days or longer. In an exemplary embodiment, the active agent according to Formula I is deoxyarbutin and the degradation product is hydroquinone.

The term "physical stability" means that the formulation does not separate into phases during storage. Furthermore, the term "physical stability" especially means that the compositions do not show any significant changes in macroscopic appearance, in particular of color, or in microscopic appearance, and no significant change in viscosity over time and at temperatures of from about 4 to about 40° C. for at least about 7 days, at least about 30 days, at least about 45 days, at least about 60 days, at least about 90 days or longer. An exemplary formulation takes on a light yellow tone on storage at temperatures above room temperature for the time specified above.

Throughout the present disclosure, the term "room temperature" means a temperature from about 20° C. to about 30° C.

"Dermatologically acceptable carrier" (which may be referred to as "carrier"), as this term is used herein refers to a component of the compositions of the present invention for the composition. The phrase "dermatologically acceptable carrier", as used herein, means that the carrier is suitable for topical application to the keratinous tissue, has good aesthetic properties, is compatible with the skin tone agents in the composition, and will not cause any unreasonable safety or toxicity concerns. A suitable carrier is selected to yield a desired product form. Furthermore, the solubility or dispersibility of the components may dictate the form and character of the carrier. In one embodiment, the carrier is present at a level of from about 50 wt % to about 99 wt %, about 60 wt % to about 98 wt %, about 70 wt % to about 98 wt %, or, alternatively, from about 80 wt % to about 95 wt %, by weight of the composition. In another embodiment, the carrier is present in the skin care composition at a level of from about 2 wt % to about 50 wt %, e.g., from about 25 wt % to about 50 wt %, which may be diluted upon application with a suitable carrier diluent.

The carrier can be in a wide variety of forms. Non-limiting examples include simple solutions (e.g., organic solvent, or oil based), emulsions, and solid forms (e.g., gels, sticks, flowable solids, or amorphous materials). In certain embodiments, the dermatologically acceptable carrier is in the form of an emulsion. The oily phase of the present invention may comprise silicone oils, non-silicone oils such as hydrocarbon oils, esters, ethers, and the like, and mixtures thereof.

Acceptable carriers that may be used in the dermatologically acceptable carrier include, but are not limited to alcohols, such as ethanol, propanol and isopropanol. In an exemplary embodiment, such a carrier is an "oily phase" and, optionally, includes only the alcohol.

Emulsions may further comprise an emulsifier. The composition may comprise any suitable percentage of emulsifier to sufficiently emulsify the carrier. Suitable weight ranges include from about 0.1 wt % to about 10 wt % or about 0.2 wt % to about 5 wt % of an emulsifier, based on the weight of the composition. Emulsifiers may be nonionic, anionic or cationic. Suitable emulsifiers are disclosed in, for example, U.S. Pat. No. 3,755,560, U.S. Pat. No. 4,421,769, and McCutcheon's Detergents and Emulsifiers, North American Edition, pages 317-324 (1986), which are incorporated herein by reference in their entirety. Suitable emulsions may have a wide range of viscosities, depending on the desired product form.

The term "oil" includes diverse oils. Suitable oils are, for example, Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols and/or esters of branched $C_6$-$C_{13}$-carboxylic acids with linear or branched $C_6$-$C_{22}$-fatty alcohols, such as, for example, petrolatum, sorbitol, hyaluronic acid, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkyl hydroxycarboxylic acids with linear or branched $C_6$-$C_{22}$-fatty alcohols in particular dioctyl malates, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as, for example, dicaprylyl carbonate (Cetiol® CC), Guerbet carbonates based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or unsymmetrical dialkyl ethers having 6 to 22 carbon atoms per alkyl group, such as, for example, dicaprylyl ether (Cetiol® OE), ring-opening products of epoxidized fatty acid esters with polyols, silicone oils (cyclomethicones, silicon methicone types, inter alia) and/or aliphatic or naphthenic hydrocarbons, such as, for example, squalane, squalene or dialkylcyclohexanes. Also suitable are esters of 2-propylheptanol with n-octanoate, a product which is commercially available under the tradename Cetiol® Sensoft (Cognis GmbH). Also suitable are hydrocarbons, such as for example undecan and tridecan. Also suitable are alkanes, such as for example INCI Coconut/Palm/Palm Kernel Oil Alkanes, commercially available as Vegelight 1214 from Biosynthesis).

Other oils include plant oils, such as castor oil, the sweet almond oil, olive oil, simmondsia chinensis, or the sesame oil; silicone oils such as the cyclomethicone, dimethicone, caprylyl methicone; mineral oils such as isohexadecane; polyisobutene; hydrogenated polyisobutene; light mineral oil; and propylparaben.

Exemplary oils include triglycerides, such as the caprylic/capric triglycerides or derivatives such as PEG-8 caprylic/capric triglycerides; esters, such as the octyldodecyl myristate, the $C_{12}$-$C_{15}$ alkyl benzoate; cetearyl isononanoate; diisopropyl adipate; isononyl isononanoate; ascorbyl palmitate; isopropyl palmitate; octyldodecyl neopentanoate; sucrose stearate; glyceryl behenate; isopropyl isostearate; alcohols, such as: ethanol, isopropanol, propanediol; dipropylene glycol; glycerine; butylene glycol; ethoxydiglycol; ethers and derivatives, such as the PPG-15 stearyl ether; PPG-14 butyl ether, and mixtures thereof.

As will be apparent to one of skill in the art each of the components set forth above is optionally included in the fatty phase of the formulation of the invention. Further each component can be combined with another component or more than one other component in any combination.

The fatty phase of a composition according to the invention may also comprise at least one lipophilic gelling agent or thickener depending on the desired viscosity. Specifically, these compounds are used in the present invention as "viscosity regulators".

According to the invention, the term "lipophilic thickeners or gelling agents" means compounds chosen especially from waxes, hydrogenated oils and fatty acid esters, silica derivatives (e.g., Silica Dimethyl Silylate).

The term "wax" generally means a lipophilic compound, which is solid at room temperature (25° C.), with a reversible solid/liquid change of state, which has a melting point of greater than or equal to 30° C., which may be up to 200° C. and especially up to 120° C. As waxes that may be used, mention may be made of carnauba wax, microcrystalline waxes, beeswax, sold under the name Cerabeil blanche by Barlocher, glyceryl behenate, derivatives thereof such as glyceryl monobehenate, glyceryl dibehenate, tribehenine or a mixture thereof, such as that sold under the name Compritol 888 by Gattefossé, or candelilla wax. The term "hydrogenated oil" means oils obtained by catalytic hydrogenation of animal or plant oils containing linear or branched $C_8$-$C_{32}$ fatty chains. Among these oils, mention may be made especially of hydrogenated jojoba oil, isomerized jojoba oil such as partially hydrogenated trans-isomerized jojoba oil manufactured or sold by the company Desert Whale under the commercial reference Iso-Jojoba-50®, hydrogenated sunflower oil, the hydrogenated castor oil sold especially under the name Cutina HR by Cognis, the polyoxyethylenated castor oil sold especially under the name Cremophor EL by BASF, hydrogenated coconut oil and hydrogenated lanolin oil; hydrogenated castor oil will preferably be used. As fatty acid esters that may be used, mention may be made of lanolin sold especially under the name Medilan by Croda, the fatty acid esters of glycerol sold under the name Gelucire by Gattefossé, the hydrogenated coconut glycerides sold under the name Akosoft 36 by Karlshamns, or the diethylene glycol or propylene glycol monostearate sold, respectively, under the names Hydrine or Monostéol by Gattefossé. The amount of lipophilic thickeners or gelling agents in the composition according to the invention is generally from about 1% to about 40% and preferably from about 5% to about 30% by weight relative to the total weight of the composition.

The term "butter" generally means extracts from plants or herbs, such as Cocoa butter, Kokum butter, Mango butter, Sal butter, Shea butter, Aloe vera butter, Lemon butter, Strawberry butter, Satsuma butter, Olive butter, Vitamin E butter, Moringa butter, Grapefruit butter. The amount of butter in the composition according to the invention is generally from about 1% to about 40% and preferably from about 2% to about 30% by weight relative to the total weight of the composition The composition of the invention may contain an elastomer. The term "elastomer" means any polyorganosiloxane elastomer, i.e., any chemically crosslinked siloxane polymer that has viscoelastic properties especially such as, preferably, the Elastomer 10 sold by Dow Corning. The amount of high molecular weight elastomer in the composition according to the invention is generally from about 0% to about 40% and preferentially from about 0 to about 20% by weight relative to the total weight of the composition.

Optionally, the composition according to the invention may also comprise at least one more surfactant and/or at least one binder.

Exemplary surfactants used are preferably nonionic surfactants, which are used for example, but not exclusively, to facilitate the incorporation of certain constituents such as glycols into the oily phase of the composition.

Among the surfactants that may be used according to the invention, mention is made of non-ionic surfactants, anionic surfactants, cationic surfactants and lipophilic surfactants.

The term "lipophilic surfactant" more particularly means: polyoxyethylenated castor oil derivatives, for instance PEG-35 castor oil, polyoxyethylenated derivatives of fatty acid esters, for instance PEG-8 caprylic capric triglycerides.

Exemplary surfactants may be esters of glycerol and optionally of polyethylene glycol, such as the mixture of glyceryl stearate and of PEG-100 stearate, sold under the name Arlacel 165 by Uniqema, the mixture of glyceryl stearate and of PEG-75 stearate sold under the name Gelot 64 by Gattefossé, the glyceryl stearate sold under the name Cutina GMSV by Cognis; emulsifying waxes, such as the self-emulsifying wax sold under the name Polawax NF by Croda or the PEG-8 beeswax sold under the name Apifil by Gattefossé; the polysorbate 80 sold under the name Tween 80 by Uniqema; the polyoxyethylenated castor oil from BASF sold especially under the trade name Cremophor EL or the mixture of glyceryl stearate and PEG-2 stearate, sold under the name Sedefos 75 by Gattefossé. The amount of surfactants in the composition according to the invention is from about 0.1% to about 10% by weight and preferably from about 1% to about 10% by weight.

Typical examples of anionic surfactants are soaps, alkylbenzenesulphonates, alkanesulphonates, olefinsulphonates, alkyl ether sulphonates, glycerol ether sulphonates, α-methyl ester sulphonates, sulpho fatty acids, alkyl sulphates, alkyl ether sulphates, glycerol ether sulphates, fatty acid ether sulphates, hydroxy mixed ether sulphates, monoglyceride (ether) sulphates, fatty acid amide(ether) sulphates, mono- and dialkyl sulphosuccinates, mono- and dialkyl sulphosuccinamates, sulphotriglycerides, amide soaps, ether carboxylic acids and salts thereof, fatty acid isethionates, fatty acid sarcosinates, fatty acid taurides, N-acylaminoacids, such as, for example, acyl lactylates, acyl tartrates, acyl glutamates and acyl aspartates, alkyl oligoglucoside sulphates, protein fatty acid condensates (in particular wheat-based vegetable products) and alkyl(ether) phosphates. If the anionic surfactants comprise polyglycol ether chains, these can have a conventional homologue distribution, but preferably have a narrowed homologue distribution. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partially oxidized alk(en)yl oligoglycosides and glucoronic acid derivatives, fatty acid N-alkylglucamides, protein hydrolysates (in particular wheat-based vegetable products), polyol fatty acid esters, sugar esters, sorbitan esters, polysorbates and amine oxides. If the nonionic surfactants contain polyglycol ether chains, these can have a conventional homologue distribution, but preferably have a narrowed homologue distribution.

Typical examples of cationic surfactants are quaternary ammonium compounds, such as, for example, dimethyldistearylammonium chloride, and ester quats, in particular quaternized fatty acid trialkanolamine ester salts. Typical examples of amphoteric and zwitterionic surfactants are alkylbetaines, alkylamidobetaines, aminopropionates, aminoglycinates, imidazoliniumbetaines and sulphobetaines. The specified surfactants are exclusively known compounds. Typical examples of particularly suitable mild, i.e., particularly skin-compatible, surfactants are fatty alcohol polyglycol ether sulphates, monoglyceride sulphates, mono- and/or dialkyl sulphosuccinates, fatty acid isethionates, fatty acid sarcosinates, fatty acid taurides, fatty acid glutamates, α-olefinsulphonates, ether carboxylic acids, alkyl oligoglucosides, fatty acid glucamides, alkylamidobetaines, amphoacetals and/or protein fatty acid condensates, the latter preferably being based on wheat proteins.

As will be apparent to one of skill in the art each of the components set forth above is optionally included in the fatty phase of the formulation of the invention. Further each component can be combined with another component or more than one other component in any combination.

Exemplary formulations of the invention include at least one oily phase that is a solvent for the active agent. It may also comprise at least one fatty phase that is a non-solvent for the active agent. Exemplary formulations include an oily phase that is a solvent for the active agent and a fatty phase that is not a solvent for the active agent; alternatively, the composition comprises only an oily phase that is a solvent for the active agent. The amount of solvent fatty phase in the composition according to the invention is generally from about 1% to about 99%, e.g., from about 5% to about 98% by weight relative to the total weight of the composition.

EXEMPLARY EMBODIMENTS

In various embodiments, the present invention provides essentially anhydrous compositions comprising monoethers of dihydroxybenzene in a dermatologically acceptable carrier, and optionally at least one additional active agent.

In an exemplary embodiment, the present invention provides a cosmetic or pharmaceutical dermatological formulation of use in depigmenting skin or otherwise lightening the tone of skin to which it is applied. In an exemplary embodiment, the active depigmenting ingredient has a structure according to Formula (I):

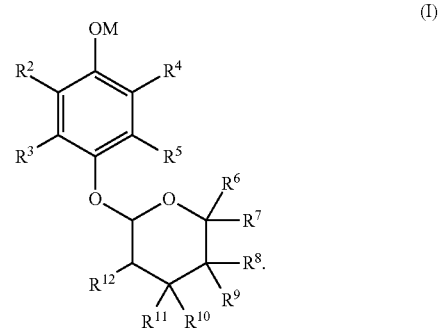

In Formula (I) $R^1$, $R^2$, $R^3$, $R^4$, $R^5$, $R^6$, $R^7$, $R^8$, $R^9$, $R^{10}$, $R^{11}$, and $R^{12}$ are independently selected from H, substituted or unsubstituted alkyl, substituted or unsubstituted heteroalkyl, substituted or unsubstituted aryl, substituted or unsubstituted heteroaryl, halogen, CN, $CF_3$, acyl, $—SO_2NR^{13}R^{14}$, $—NR^{13}R^{14}$, $—OR^{13}$, $—S(O)_2R^{13}$, $—C(O)R^{13}$, $—COOR^{13}$, $—CONR^{13}R^{14}$, $—S(O)_2OR^{13}$, $—OC(O)R^{13}$, $—C(O)$ NR$^{13}$R$^{14}$, —NR$^{13}$C(O)R$^{14}$, —NR$^{13}$SO$_2$R$^{14}$, NR$^{13}$C(O) NR$^{14}$R$^{15}$, C(NR$^{13}$)R$^{10}$, and —NO$_2$, wherein two or more of R$^1$, R$^2$, R$^3$, R$^4$, R$^5$, R$^6$, R$^7$, R$^8$, R$^9$, R$^{10}$, R$^{11}$, and R$^{12}$, together with the atoms to which they are bonded, are optionally joined to form a ring system which is a member selected from substituted or unsubstituted cycloalkyl, substituted or unsubstituted heterocycloalkyl, substituted or unsubstituted aryl and substituted or unsubstituted heteroaryl.

In various embodiments, R$^{13}$, R$^{14}$, and R$^{15}$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, and two or more of R$^{13}$, R$^{14}$, and R$^{15}$, together with the atoms to which they are bonded, are optionally joined to form a 5- to 7-membered ring which is a member selected from substituted or unsubstituted cycloalkyl, substituted or unsubstituted heterocycloalkyl, substituted or unsubstituted aryl and substituted or unsubstituted heteroaryl.

M is H or a counterion component of a salt of a phenol. Exemplary counterions are those found in dermatologically acceptable salts as this term is discussed herein.

In an exemplary embodiment, the active agent according to Formula (I) is deoxyarbutin. In an exemplary embodiment, the active agent is deoxyarbutin and the formulation is essentially free of hydroquinone, either added or produced by degradation of the deoxyarbutin to hydroquinone.

In various embodiments, the formulation is essentially anhydrous and includes an alcohol oily phase in which the active agent according to Formula (I) is dissolved. The alcohol oily phase is incorporated into a dermatologically acceptable carrier (e.g., a fatty phase), such as a gel, paste, cream, etc. In various embodiments, the carrier includes one or more organosilicone compounds. The oily phase is incorporated in the fatty phase by suspension, dispersion, emulsification and the like. In an exemplary embodiment, the active agent is not substantially soluble in the fatty phase.

The formulations of the invention have a pH ranging from about 3.0 to about 10, which may be measured by taking a direct pH measurement using a standard hydrogen electrode of the composition at 25° C. Accordingly, the pH of the skin care composition may be within the range from about 6 to about 9, for example. An exemplary essentially anhydrous formulation of the invention has a pH of less than or equal to about 8.

The anhydrous nature of the composition according to the invention makes it possible to avoid the instability of the phenolic derivative (e.g., Formula (I)), in particular its aqueous hydrolysis and oxidation in aqueous medium. In an exemplary embodiment, the active agent according to Formula I is deoxyarbutin and its degradation to hydroquinone is retarded or prevented by the anhydrous nature of the formulation.

In an exemplary embodiment, no more than about 0.01% by weight of the total formulation is degraded active agent. In various embodiments, not more than about 0.02% of the formulation is degraded active agent. In an exemplary embodiment, the active agent is deoxyarbutin and the degradation product is hydroquinone.

In an exemplary embodiment, the degradation product of the active agent of Formula (I) is hydroquinone and hydroquinone is present in the formulation in an amount of less than about 20 ppm after storage as measured using High Performance Liquid Chromatography (HPLC). An exemplary HPLC method is that for hydroquinone, e.g., "Hygenic Standard for Cosmetics, Chinese Food and Drug Administration, 2007 Edition, 215-220.

Exemplary formulations of the invention include two or more components discussed hereinbelow in any combination. In an exemplary embodiment, the formulation of the invention includes a component effective at binding, film forming, and viscosity control (e.g., Polyisobutene (H300)) in an amount of from about 5 wt % to about 15 wt %, e.g., about 10 wt %. In an exemplary embodiment, the formulation of the invention includes a component effective as an emollient, a solvent, and a perfume, e.g., isododecane, in an amount of from about 20 wt % to about 30 wt %, e.g., about 24 wt %. In an exemplary embodiment, the formulation of the invention includes a component that is effective as an emollient, a hair conditions, a skin conditioner and as a solvent (e.g., cyclopentasiloxane) in an amount of from about 20 wt % to about 30 wt %, e.g., about 24 wt %. In an exemplary embodiment, the formulation of the invention includes a component effective as a conditioning agent, e.g., PPG-14 butyl ether, in an amount from about 6 wt % to about 9 wt %, e.g., about 7 wt %, e.g., about 7.3 wt %. In an exemplary embodiment, the formulation of the invention includes a component that is effective as an emollient, masking, skin conditioning agent with solvent and perfuming properties, e.g., caprylic/caprictriglyceride in an amount of from about 5 wt % to about 15 wt %, e.g., 10 wt %. In an exemplary embodiment, the formulation of the invention includes a component that functions as a preservative, e.g., benzyl alcohol in an amount of from about 0.1 wt % to about 1 wt %, e.g., about 0.50 wt %. In an exemplary embodiment, the formulation of the invention includes a component that functions as an antioxidant and conditioning agent, e.g., tocopheryl acetate, in an amount of from about 0.01 wt % to about 0.1 wt %, e.g., 0.05 wt %. In an exemplary embodiment, the formulation of the invention includes a component with skin conditioning properties, e.g, caprylyl methicone, in an amount of from about 4 wt % to about 10 wt %, e.g., about 7 wt %. In an exemplary embodiment, the formulation of the invention includes a component that has anticaking, antifoaming, emollient, emulsion stabilizing and viscosity controlling properties, e.g., silica dimethyl silylate, in an amount of from about 1 wt % to about 5 wt %, e.g., about 3 wt %. In an exemplary embodiment, the formulation of the invention includes one or more independently selected antioxidant, e.g., BHT, ascorbyl palmitates and combinations thereor, each in an amount of from about 0.05 wt % to about 0.15 wt %. In an exemplary embodiment, the formulation of the invention includes a dermatologically active depigmenting agent, e.g., tetrahydropyranyloxy phenol, in an amount of from about 1 wt % to about 10 wt %, e.g., about 6 wt %. In an exemplary embodiment, the formulation of the invention includes a component having antifoaming, solvent, viscocity controlling and perfuming properties, e.g., isopropyl alcohol, in an amount of from about 5 wt % to about 10 wt %. In an exemplary embodiment, the formulation of the invention includes a perfume in an amount of from about 0.1 wt % to about 0.3 wt %.

An exemplary formulation of the invention includes the components in the amounts set forth in Table 1.

TABLE 1

| INCI NOMENCLATURE | FUNCTION | % In Serum |
|---|---|---|
| Polyisobutene (H300) | binding, film forming, viscosity controlling | ~10 wt % |
| Isododecane | emollient, solvent, perfuming | ~24 wt % |
| cyclopentasiloxane | emollient, hair conditioning, skin conditioning, solvent | ~24 wt % |
| PPG-14 Butyl Ether | conditioning agent-miscellaneous | ~7.3 wt % |
| Caprylic/Caprictriglyceride | emollient, masking, skin conditioning, solvent, perfuming | ~10 wt % |
| Benzyl Alcohol | preservative | ~0.5 wt % |
| Tocopheryl Acetate | antioxidant; conditioning agent-miscellaneous | ~0.05 wt % |
| Caprylyl Methicone | skin conditioning | ~7 wt % |
| Silica Dimethyl Silylate | anticaking, antifoaming, emollient, emulsion stabilising, viscosity controlling | ~3 wt % |
| BHT | antioxidant | ~0.20% |
| Tetrahydropyranyloxy Phenol | depigmenting | ~6 wt % |
| perfume | perfuming | ~0.2 wt % |

In one exemplary mode, the composition comprises:

an active phase comprising, as a dermatological active agent, a compound according to Formula (I), and at least one solvent for the active agent;

a non-active phase containing at least one fatty-phase thickener, e.g., glyceryl behenate and derivatives, and optionally an additional lipophilic thickener, and/or at least one oil and/or at least one lipophilic surfactant;

and/or at least one oil and/or at least one lipophilic emollient, and/or a binder, and/or any optional additive.

In another exemplary mode according to the invention, the composition comprises:

an active phase comprising, as a dermatological active agent, a compound according to Formula (I), and at least one solvent for the active agent;

a non-active phase containing at least one fatty-phase thickener, e.g., glyceryl behenate and derivatives, and optionally an additional lipophilic thickener, and/or at least one oil, and/or at least one lipophilic surfactant, and/or a binder, and/or any optional additive; a polyorganosiloxane elastomer.

The composition according to the invention comprises a solvent or mixture of solvents for the active agent. Exemplary solvent(s) is/are alcohol and account for a maximum of about 20% (by weight relative to the total weight of the composition) of alcohol solvent, e.g., isopropanol, ethanol, propanediol, dipropylene glycol. In the composition according to the invention, this amount of solvent, combined with the oils and other carrier elements present, is sufficient to dissolve the desired concentrations of active agent and to obtain physically and chemically stable preparations. Exemplary alcohols are essentially anhydrous.

In an exemplary embodiment, the composition according to the invention comprises, on a weight basis relative to the total weight:

from about 0.01% to about 20% of at least one pharmaceutical active agent of phenolic derivative type, e.g., according to Formula I;

from about 0.05% to about 99% of solvent oily phase and/or lipophilic surfactants;

from about 0 to about 50% of additional lipophilic gelling agents or thickeners;

from about 0 to about 20% of additives.

In various embodiments, the composition according to the invention comprises, on a weight basis relative to the total weight:

from about 0.05% to about 6% of at least one phenolic derivative, of polyphenol type;

from about 1% to about 50% of solvent oily phase and/or lipophilic surfactants;

from about 1% to about 40% of additional lipophilic gelling agents or thickeners;

from about 0 to about 20% of surfactants;

from about 0 to about 30% of binder(s);

from about 0 to about 10% of additives. In various embodiments, the composition according to the invention comprises, on a weight basis relative to the total weight:

from about 1% to about 50% of solvent oily phase and/or lipophilic surfactants;

from about 10% to about 25% of glyceryl behenate;

from about 0 to about 10% of surfactants;

from about 0 to about 20% of binder(s);

from about 0 to about 10% of additives.

The anhydrous composition according to the invention may be in the various known galenical forms, which a person skilled in the art will adapt to the particular use of the composition, see, e.g., Dermatologically Acceptable Salt, herein.

Via the topical route, the compositions may be in any galenical form normally used for topical administration. As non-limiting examples of topical compositions mention may be made of compositions as described in the American pharmacopoeias (USP32-NF27—Chap <1151>—Pharmaceutical Dosage Forms) or European pharmacopoeias (Edition 6.3 in the chapter: Preparations semi-solides pour application cutanée [Semi-solid preparations for cutaneous application]) or as defined in the decision trees of the American Food and Drug Administration (FDA) (CDER Data Standards Manual Definitions for topical dosage Forms). The compositions according to the invention may thus be in liquid, semi-solid, pasty or solid form, and more particularly in the form of ointments, oily solutions, dispersions of the lotion type, which may be two-phase lotions, serum, anhydrous or lipophilic gels, powders, impregnated pads, syndets, wipes, sprays, mousses, sticks, shampoos, compresses, washing bases, emulsions of liquid or semi-liquid consistency of the oil-in-glycol or glycol-in-oil type, a microemulsion, semi-liquid or solid suspensions or emulsions of the white or coloured cream type, gel or pomade, suspensions of microspheres or nanospheres or of lipid or polymeric vesicles, or microcapsules, microparticles or nanoparticles, or polymeric or gelled patches for controlled release.

In one exemplary mode according to the invention, the composition is an anhydrous pharmaceutical or cosmetic composition of ointment type. The FDA defines an ointment as being a semi-solid composition comprising, as vehicle, less than 20% water and volatile compounds and more than 50% hydrocarbons, waxes or polyols. In certain cases, when the content of volatiles is high, such compositions may be referred to as creams (decision tree of the American Food and Drug Administration (FDA)). The American Pharmacopoeia defines an ointment as being a product whose base is a vehicle that may belong to the following four classes: hydrocarbon base or absorbent base or water-washable base or water-soluble base. The European Pharmacopoeia defines an ointment as being a one-phase composition in which liquids or solids may be dispersed.

The ointment according to the invention is preferentially a composition that is thick at room temperature, which comprises from about 80% to about 98% by weight, relative to the total weight of the composition, of hydrophobic compounds other than petroleum jelly. Such compounds are chosen from, e.g., liquid oils alone or as a mixture, the said oils possibly being hydrocarbons, esters, plant oils and/or silicone oils, which are volatile or non-volatile, which may be gelled with lipophilic compounds that are solid at room temperature such as waxes, butters or fatty acid esters.

The formulations of the invention can be characterized by any art-recognized method. Optionally, a measurement of the flow threshold may be performed in order to characterize the finished product. For the measurement of the flow threshold, a VT550 Haake rheometer with an SVDIN measuring spindle was used.

The rheograms are produced at 25° C. at an imposed speed of 0 to 100 s$^{-1}$. The viscosity values are given at shear values of 4 s$^{-1}$, 20 s$^{-1}$, 100 s$^{-1}$ ($\gamma$). The term "flow threshold" ($\tau_0$ expressed in Pascals) means the force (minimum shear stress) required to overcome the cohesion forces of Van der Waals type and to bring about flow.

Exemplary Additives

As set forth hereinabove, the formulations of the invention may include one or more additives other than those components set forth in the exemplary formulations. Emulsifiers: For example, nonionogenic surfactants from at least one of the following groups: addition products of from about 2 to about 30 wt % of ethylene oxide and/or about 0 to about 5 wt % of propylene oxide to linear fatty alcohols having 8 to 22 carbon atoms, to fatty acids having 12 to 22 carbon atoms, to alkylphenols having 8 to 15 carbon atoms in the alkyl group, and alkylamines having 8 to 22 carbon atoms in the alkyl radical; alkyl and/or alkenyl oligoglycosides having 8 to 22 carbon atoms in the alk(en)yl radical and the ethoxylated analogues thereof; addition products of from 1 to 15 wt % of ethylene oxide to castor oil and/or hydrogenated castor oil; addition products of from 15 to 60 wt % of ethylene oxide to castor oil and/or hydrogenated castor oil; partial esters of glycerol and/or sorbitan with unsaturated, linear or saturated, branched fatty acids having 12 to 22 carbon atoms and/or hydroxycarboxylic acids having 3 to 18 carbon atoms, and the adducts thereof with 1 to 30 wt % of ethylene oxide; partial esters of polyglycerol (average degree of self-condensation 2 to 8), polyethylene glycol (molecular weight 400 to 5000), trimethylolpropane, pentaerythritol, sugar alcohols (e.g. sorbitol), alkyl glucosides (e.g. methyl glucoside, butyl glucoside, lauryl glucoside), and polyglucosides (e.g. cellulose) with saturated and/or unsaturated, linear or branched fatty acids having 12 to 22 carbon atoms and/or hydroxycarboxylic acids having 3 to 18 carbon atoms, and the adducts thereof with 1 to 30 wt % of ethylene oxide; mixed esters of pentaerythritol, fatty acids, citric acid and fatty alcohol and/or mixed esters of fatty acids having 6 to 22 carbon atoms, methylglucose and polyols, preferably glycerol or polyglycerol, mono-, di- and trialkyl phosphates, and mono-, di- and/or tri-PEG alkyl phosphates and salts thereof; wool wax alcohols; polysiloxane-polyalkyl-polyether copolymers and corresponding derivatives; block copolymers, e.g. polyethylene glycol-30 dipolyhydroxystearates; polymer emulsifiers, e.g. Pemulen grades (TR-1, TR-2) from Goodrich; polyalkylene glycols, and glycerol carbonate.

Ethylene Oxide Addition Products. The addition products of ethylene oxide and/or of propylene oxide to fatty alcohols, fatty acids, alkylphenols or to castor oil are known, commercially available products. These are homologue mixtures whose average degree of alkoxylation corresponds to the ratio of the amounts of substance of ethylene oxide and/or propylene oxide and substrate with which the addition reaction is carried out. C$_{12/18}$-fatty acid mono- and diesters of addition products of ethylene oxide to glycerol are known as refatting agents for cosmetic preparations.

Alkyl and/or Alkenyl Oligoglycosides. Alkyl and/or alkenyl oligoglycosides, their preparation and their use are known from the prior art. They are prepared, in particular, by reacting glucose or oligosaccharides with primary alcohols having 8 to 18 carbon atoms. With regard to the glycoside radical, both monoglycosides, in which a cyclic sugar radical is glycosidically bonded to the fatty alcohol, and also oligomeric glycosides having a degree of oligomerization of up to, preferably, about 8, are suitable. The degree of oligomerization here is a statistical average value which is based on a homologue distribution customary for such technical-grade products.

Partial Glycerides. Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride, and the technical-grade mixtures thereof which may also comprise small amounts of triglyceride as a minor product of the preparation process. Likewise suitable are addition products of about 1 to about 30 wt %, preferably about 5 to about 10 wt %, of ethylene oxide to said partial glycerides.

Sorbitan Esters. Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate, and technical-grade mixtures thereof. Likewise suitable are addition products of from 1 to 30 wt %, preferably 5 to 10 wt %, of ethylene oxide to said sorbitan esters.

Polyglycerol Esters. Typical examples of suitable polyglycerol esters are polyglyceryl-2 dipolyhydroxystearate (Dehymuls® PGPH), polyglycerol-3 diisostearate (Lameform® TGI), polyglyceryl-4isostearate (Isolan® GI 34), polyglyceryl-3 oleate, diisostearoyl polyglyceryl-3diisostearate (Isolan® PDI), polyglyceryl-3 methylglucose distearate (Tego Care® 450), polyglyceryl-3 beeswax (Cera Bellina®), polyglyceryl-4 caprate (Polyglycerol Caprate T2010/90), polyglyceryl-3 cetyl ether (Chimexane® NL), polyglyceryl-3 distearate (Cremophor® GS 32) and polyglyceryl polyricinoleate (Admul® WOL 1403), polyglyceryl dimerate isostearate, and mixtures thereof. Examples of further suitable polyol esters are the mono-, di- and triesters, optionally reacted with 1 to 30 wt % of ethylene oxide, of trimethylolpropane or pentaerythritol with lauric acid, coconut fatty acid, tallow fatty acid, palmitic acid, stearic acid, oleic acid, behenic acid and the like.

Anionic Emulsifiers. Typical anionic emulsifiers are aliphatic fatty acids having 12 to 22 carbon atoms, such as, for example, palmitic acid, stearic acid or behenic acid, and dicarboxylic acids having 12 to 22 carbon atoms, such as, for example, azelaic acid or sebacic acid.

Amphoteric and Cationic Emulsifiers. Furthermore, zwitterionic surfactants can be used as emulsifiers. The term "zwitterionic surfactants" refers to those surface-active compounds which carry at least one quaternary ammonium group and at least one carboxylate and one sulphonate group in the molecule. Particularly suitable zwitterionic surfactants are the so-called betaines, such as N-alkyl-N,N-dimethylammonium glycinates, for example cocoalkyldimethylammonium glycinate, N-acylaminopropyl-N,N-dimethylammonium glycinates, for example cocoacylaminopropyl-dimethylammonium glycinate, and 2-alkyl-3-carboxymethyl-3-hydroxyethylimidazolines having in each case 8 to 18 carbon atoms in the alkyl or acyl group, and cocoacylaminoethylhydroxyethylcarboxymethyl glycinate. Particular preference is given to the fatty acid amide derivative known under the CTFA name Cocamidopropyl Betaine. Likewise suitable emulsifiers are ampholytic surfactants. The term "ampholytic surfactants" means those surface-active compounds which, apart from a $C_{8/18}$-alkyl or -acyl group, contain at least one free amino group and at least one —COOH or —SO$_3$H group in the molecule and are capable of forming internal salts. Examples of suitable ampholytic surfactants are N-alkylglycines, N-alkylaminopropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case about 8 to 18 carbon atoms in the alkyl group. Particularly preferred ampholytic surfactants are N-cocoalkylaminopropionate, cocoacylaminoethylaminopropionate and $C_{12/18}$-acylsarcosine. Finally, cationic surfactants are also suitable as emulsifiers, those of the ester quat type, preferably methyl-quaternized difatty acid triethanolamine ester salts, being particularly preferred.

In one embodiment of the invention the cosmetic composition further comprises at least one fat or wax.

Typical examples of fats are glycerides, i.e. solid or liquid vegetable or animal products which consist essentially of mixed glycerol esters of higher fatty acids, suitable waxes are inter alia natural waxes, such as, for example, candelilla wax, carnauba wax, Japan wax, esparto grass wax, cork wax, guaruma wax, rice germ oil wax, sugarcane wax, ouricury wax, montan wax, beeswax, shellac wax, spermaceti, lanolin (wool wax), uropygial grease, ceresin, ozokerite (earth wax), petrolatum, paraffin waxes, microcrystalline waxes; chemically modified waxes (hard waxes), such as, for example, montan ester waxes, sasol waxes, hydrogenated jojoba waxes, and synthetic waxes, such as, for example, polyalkylene waxes and polyethylene glycol waxes. In addition to the fats, suitable additives are also fat-like substances, such as lecithins and phospholipids. The term lecithins is understood by the person skilled in the art as meaning those glycerophospholipids which are founded from fatty acids, glycerol, phosphoric acid and choline by esterification. Lecithins are thus also often as phosphatidylcholines (PC) in the specialist world. Examples of natural lecithins which may be mentioned are the cephalins, which are also referred to as phosphatidic acids and constitute derivatives of 1,2-diacyl-sn-glycerol-3-phosphoric acids. By contrast, phospholipids are usually understood as meaning mono- and preferably diesters of phosphoric acid with glycerol (glycerol phosphates), which are generally classed as fats. In addition, sphingosines or sphingolipids are also suitable.

In one embodiment of the invention the cosmetic composition further comprises at least one pearlescent wax.

Examples of suitable pearlescent waxes are: alkylene glycol esters, specifically ethylene glycol distearate; fatty acid alkanolamides, specifically coconut fatty acid diethanolamide; partial glycerides, specifically stearic acid monoglyceride; esters of polybasic, optionally hydroxy-substituted carboxylic acids with fatty alcohols having 6 to 22 carbon atoms, specifically long-chain esters of tartaric acid; fatty substances, such as, for example, fatty alcohols, fatty ketones, fatty aldehydes, fatty ethers and fatty carbonates, which have a total of at least 24 carbon atoms, specifically laurone and distearyl ether; fatty acids, such as stearic acid, hydroxystearic acid or behenic acid, ring-opening products of olefin epoxides having 12 to 22 carbon atoms with fatty alcohols having 12 to 22 carbon atoms and/or polyols having 2 to 15 carbon atoms and 2 to 10 hydroxyl groups, and mixtures thereof.

In one embodiment of the invention the cosmetic composition further comprises at least one consistency regulator and/or thickener.

Suitable consistency regulators are primarily fatty alcohols or hydroxy fatty alcohols having 12 to 22, and preferably 16 to 18, carbon atoms, and also partial glycerides, fatty acids or hydroxy fatty acids. Preference is given to a combination of these substances with alkyl oligo-glucosides and/or fatty acid N-methylglucamides of identical chain length and/or polyglycerol poly-12-hydroxystearates. Suitable thickeners are, for example, Aerosil grades (hydrophilic silicas), polysaccharides, in particular xanthan gum, guar guar, agar agar, alginates and tyloses, carboxymethylcellulose, hydroxyethylcellulose and hydroxypropylcellulose, and also relatively high molecular weight polyethylene glycol mono- and diesters of fatty acids, polyacrylates (e.g. Carbopols® and Pemulen grades from Goodrich; Synthalens® from Sigma; Keltrol grades from Kelco; Sepigel grades from Seppic; Salcare grades from Allied Colloids), polyacrylamides, polymers, polyvinyl alcohol and polyvinylpyrrolidone. Bentonites, such as, for example, Bentone® Gel VS 5PC (Rheox), which is a mixture of cyclopentasiloxane, disteardimonium hectorite and propylene carbonate, have also proven to be particularly effective. Also suitable are surfactants, such as, for example, ethoxylated fatty acid glycerides, esters of fatty acids with polyols such as, for example, pentaerythritol or trimethylolpropane, fatty alcohol ethoxylates having a narrowed homologue distribution or alkyl oligoglucosides, and electrolytes such as sodium chloride and ammonium chloride.

In one embodiment of the invention the cosmetic composition further comprises at least one superfatting agent.

Superfatting agents which can be used are substances such as, for example, lanolin and lecithin, and polyethoxylated or acylated lanolin and lecithin derivatives, polyol fatty acid esters, monoglycerides and fatty acid alkanolamides, the latter also serving as foam stabilizers.

In one embodiment of the invention the cosmetic composition further comprises at least one stabilizer.

Stabilizers which can be used are metal salts of fatty acids, such as, for example, magnesium, aluminium and/or zinc stearate or ricinoleate.

In one embodiment of the invention the cosmetic composition further comprises at least one polymer.

Suitable cationic polymers are, for example, cationic cellulose derivatives, such as, for example, a quaternized hydroxyethylcellulose obtainable under the name Polymer JR 400® from Amerchol, cationic starch, copolymers of diallylammonium salts and acrylamides, quaternized vinylpyrrolidone-vinylimidazole polymers, such as, for example, Luviquat® (BASF), condensation products of polyglycols and amines, quaternized collagen polypeptides, such as, for example, lauryldimonium hydroxypropyl hydrolyzed collagen (Lamequat® L/Grunau), quaternized wheat polypeptides, polyethyleneimine, cationic silicone polymers, such as, for example, amodimethicones, copolymers of adipic acid and dimethylaminohydroxy-propyldiethylenetriamine (Cartaretins®/Sandoz), copolymers of acrylic acid with dimethyldiallylammonium chloride (Merquat® 550/Chemviron), polyaminopolyamides, and crosslinked water-soluble polymers thereof, cationic chitin derivatives, such as, for example, quaternized chitosan, optionally in microcrystalline dispersion, condensation products from dihaloalkyls, such as, for example, dibromobutane with bisdialkylamines, such as, for example, bis-dimethylamino-1,3-propane, cationic guar gum, such as, for example, Jaguar® CBS, Jaguar® C-17, Jaguar® C-16 from Celanese, quaternized ammonium salt polymers, such as, for example, Mirapol® A-15, Mirapol® AD-1, Mirapol® AZ-1 from Miranol.

Suitable anionic, zwitterionic, amphoteric and nonionic polymers are, for example, vinyl acetate-crotonic acid copolymers, vinylpyrrolidone-vinyl acrylate copolymers, vinyl acetate-butyl maleate-isobornyl acrylate copolymers, methyl vinyl ether-maleic anhydride copolymers and esters thereof, uncrosslinked polyacrylic acids and polyacrylic acids crosslinked with polyols, acryl amidopropyltrimethyl ammonium chloride-acrylate copolymers, octylacrylamide-methyl methacrylate-tert-butylaminoethyl methacrylate-2-hydroxypropyl methacrylate copolymers, polyvinylpyrrolidone, vinylpyrrolidone-vinyl acetate copolymers, vinylpyrrolidone-dimethylaminoethyl methacrylate-vinylcaprolactam terpolymers, and optionally derivatized cellulose ethers and silicones.

In one embodiment of the invention the cosmetic composition further comprises at least one silicone compound. Exemplary silicone compounds are the simethicones and siloxanes (e.g., caprylyl methicone, cyclomethicone, PEG-10 dimethicone, cyclopentasiloxane).

Suitable silicone compounds are, for example, dimethylpolysiloxanes, methylphenylpolysiloxanes, cyclic silicones, and amino-, fatty acid-, alcohol-, polyether-, epoxy-, fluorine-, glycoside- and/or alkyl-modified silicone compounds, which can either be liquid or in resin form at room temperature. Also suitable are simethicones, which are mixtures of dimethicones having an average chain length of from 200 to 300 dimethylsiloxane units and hydrogenated silicates.

Silicone elastomers suitable for use in the compositions of the invention include those that are formed by addition reaction-curing, by reacting an SiH-containing diorganosiloxane and an organopolysiloxane having terminal olefinic unsaturation, or an alpha-omega diene hydrocarbon, in the presence of a platinum metal catalyst. Such elastomers may also be formed by other reaction methods such as condensation-curing organopolysiloxane compositions in the presence of an organotin compound via a dehydrogenation reaction between hydroxyl-terminated diorganopolysiloxane and SiH-containing diorganopolysiloxane or alpha omega diene; or by condensation-curing organopolysiloxane compositions in the presence of an organotin compound or a titanate ester using a condensation reaction between an hydroxyl-terminated diorganopolysiloxane and a hydrolysable organosiloxane; peroxide-curing organopolysiloxane compositions which thermally cure in the presence of an organoperoxide catalyst.

One type of elastomer that may be suitable is prepared by addition reaction-curing an organopolysiloxane having at least 2 lower alkenyl groups in each molecule or an alpha-omega diene; and an organopolysiloxane having at least 2 silicon-bonded hydrogen atoms in each molecule; and a platinum-type catalyst. While the lower alkenyl groups such as vinyl, can be present at any position in the molecule, terminal olefinic unsaturation on one or both molecular terminals is preferred. The molecular structure of this component may be straight chain, branched straight chain, cyclic, or network. These organopolysiloxanes are exemplified by methylvinylsiloxanes, methylvinylsiloxane-dimethylsiloxane copolymers, dimethylvinylsiloxy-terminated dimethylpolysiloxanes, dimethylvinylsiloxy-terminated dimethylsiloxane-methylphenylsiloxane copolymers, dimethylvinylsiloxy-terminated dimethylsiloxane-diphenylsiloxane-methylvinylsiloxane copolymers, trimethylsiloxy-terminated dimethylsiloxane-methylvinylsiloxane copolymers, trimethylsiloxy-terminated dimethylsiloxane-methylphenylsiloxane-methylvinylsiloxane copolymers, dimethylvinylsiloxy-terminated methyl(3,3,3-trifluoropropyl)polysiloxanes, and dimethylvinylsiloxy-terminated dimethylsiloxane-methyl(3,3,-trifluoropropyl)siloxane copolymers, decadiene, octadiene, heptadiene, hexadiene, pentadiene, or tetradiene, or tridiene.

Examples of suitable silicone elastomers for use in the compositions of the invention may be in the powder form, or dispersed or solubilized in solvents such as volatile or non-volatile silicones, or silicone compatible vehicles such as paraffinic hydrocarbons or esters. Examples of silicone elastomer powders include vinyl dimethicone/methicone silesquioxane crosspolymers like Shin-Etsu's KSP-100, KSP-101, KSP-102, KSP-103, KSP-104, KSP-105, hybrid silicone powders that contain a fluoroalkyl group like Shin-Etsu's KSP-200 which is a fluoro-silicone elastomer, and hybrid silicone powders that contain a phenyl group such as Shin-Etsu's KSP-300, which is a phenyl substituted silicone elastomer; and Dow Corning's DC 9506. Examples of silicone elastomer powders dispersed in a silicone compatible vehicle include dimethicone/vinyl dimethicone crosspolymers supplied by a variety of suppliers including Dow Corning Corporation under the tradenames 9040 or 9041, GE Silicones under the tradename SFE 839, or Shin-Etsu Silicones under the tradenames KSG-15, 16, 18. KSG-15 has the CTFA name cyclopentasiloxane/dimethicone/vinyl dimethicone crosspolymer. KSG-18 has the INCI name phenyl trimethicone/dimethicone/phenyl vinyl dimethicone crosspolymer. Silicone elastomers may also be purchased from Grant Industries under the Gransil trademark. Also suitable are silicone elastomers having long chain alkyl substitutions such as lauryl dimethicone/vinyl dimethicone crosspolymers supplied by Shin Etsu under the tradenames KSG-31, KSG-32, KSG-41, KSG-42, KSG-43, and KSG-44. Cross-linked organopolysiloxane elastomers useful in the present invention and processes for making them are further described in U.S. Pat. No. 4,970,252; U.S. Pat. No. 5,760,116; U.S. Pat. No. 5,654,362; and Japanese Patent Application JP 61-18708; each of which is herein incorporated by reference in its entirety. It is particularly desirable to incorporate silicone elastomers into the compositions of the invention because they provide excellent "feel" to the composition, are very stable in cosmetic formulations, and relatively inexpensive.

Also suitable for use as an oil phase structuring agent are one or more silicone gums. The term "gum" means a silicone polymer having a degree of polymerization sufficient to provide a silicone having a gum-like texture. In certain cases the silicone polymer forming the gum may be crosslinked. The silicone gum typically has a viscosity ranging from about 500,000 to 100 million cst at 25° C., preferably from about 600,000 to 20 million, more preferably from about 600,000 to 12 million cst. All ranges mentioned herein include all subranges, e.g. 550,000; 925,000; 3.5 million.

Such silicone gums may be purchased in pure form from a variety of silicone manufacturers including Wacker-Chemie or Dow Corning, and the like. Such silicone gums include those sold by Wacker-Belsil under the trade names CM3092, Wacker-Belsil 1000, or Wacker-Belsil DM 3096. A silicone gum where X is OH, also referred to as dimethiconol, is available from Dow Corning Corporation under the trade name 1401. The silicone gum may also be purchased in the form of a solution or dispersion in a silicone compatible vehicle such as volatile or nonvolatile silicone. An example of such a mixture may be purchased from Barnet Silicones under the HL-88 tradename, having the INCI name dimethicone.

Another type of oily phase structuring agent includes silicone waxes that are typically referred to as alkyl silicone waxes which are semi-solids or solids at room temperature. The term "alkyl silicone wax" means a polydimethylsiloxane having a substituted long chain alkyl (such as C16 to 30) that confers a semi-solid or solid property to the siloxane. Examples of such silicone waxes include stearyl dimethicone, which may be purchased from DeGussa Care & Surface Specialties under the tradename Abil Wax 9800 or from Dow Corning under the tradename 2503. Another example is bis-stearyl dimethicone, which may be purchased from Gransil Industries under the tradename Gransil A-18, or behenyl dimethicone, behenoxy dimethicone.

Also suitable as oil phase structuring agents are various types of polymeric compounds such as polyamides or silicone polyamides. The term silicone polyamide means a polymer comprised of silicone monomers and monomers containing amide groups In one embodiment of the invention the cosmetic composition further comprises at least one UV photoprotective filter.

UV photoprotective factors are, for example, to be understood as meaning organic substances (photoprotective filters) which are liquid or crystalline at room temperature and which are able to absorb ultraviolet rays and give off the absorbed energy again in the form of longer-wavelength radiation, e.g., heat. UVB filters can be oil-soluble or water-soluble. Examples of oil-soluble substances are: 3-benzylidenecamphor or 3-benzylidenenorcamphor and derivatives thereof, e.g. 3-(4-methylbenzylidene)camphor; 4-aminobenzoic acid derivatives, preferably 2-ethylhexyl 4-(dimethylamino)benzoate, 2-octyl 4-(dimethylamino)benzoate and amyl 4-(dimethylamino)benzoate; esters of cinnamic acid, preferably 2-ethylhexyl 4-methoxycinnamate, propyl 4-methoxycinnamate, isoamyl 4-methoxycinnamate, 2-ethylhexyl 2-cyano-3,3-phenyl-cinnamate (octocrylene); esters of salicylic acid, preferably 2-ethylhexyl salicylate, 4-isopropylbenzyl salicylate, homomethyl salicylate; derivatives of benzophenone, preferably 2-hydroxy-4-methoxybenzophenone, 2-hydroxy-4-methoxy-4'-methylbenzophenone, 2,2'-dihydroxy-4-methoxybenzo-phenone; esters of benzalmalonic acid, preferably di-2-ethylhexyl 4-methoxybenzalmalonate; triazine derivatives, such as, for example, 2,4,6-trianilino(p-carbo-T-ethyl-1'-hexyloxy)-1,3,5-triazine and octyltriazone or dioctylbutamidotriazone (Uvasorb® HEB); propane-1,3-diones, such as, for example, 1-(4-tert-butylphenyl)-3-(4'-methoxyphenyl)propane-1,3-dione; ketotricyclo(5.2.1.0)decane derivatives.

Suitable water-soluble substances are: 2-phenylbenzimidazole-5-sulphonic acid and the alkali metal, alkaline earth metal, ammonium, alkylammonium, alkanolammonium and glucammonium salts thereof; sulphonic acid derivatives of benzophenones, preferably 2-hydroxy-4-methoxybenzophenone-5-sulphonic acid and its salts; sulphonic acid derivatives of 3-benzylidenecamphor, such as, for example, 4-(2-oxo-3-bornylidenemethyl)benzenesulphonic acid and 2-methyl-5-(2-oxo-3-bornyl-idene)sulphonic acid and salts thereof.

Suitable typical UV-A filters are, in particular, derivatives of benzoylmethane, such as, for example, 1-(4'-tert-butylphenyl)-3-(4'-methoxyphenyl)propane-1,3-dione, 4-tert-butyl-4'-methoxydibenzoylmethane (Parsol® 1789), 1-phenyl-3-(4'-isopropylphenyl)propane-1,3-dione, and enamine compounds. The UV-A and UV-B filters can of course also be used in mixtures. Particularly favourable combinations consist of the derivatives of benzoylmethane, e.g. 4-tert-butyl-4'-methoxydi-benzoylmethane (Parsol® 1789) and 2-ethylhexyl 2-cyano-3,3-phenylcinnamate (octocrylene) in combination with esters of cinnamic acid, preferably 2-ethylhexyl 4-methoxycinnamate and/or propyl 4-methoxycinnamate and/or isoamyl 4-methoxycinnamate. Advantageously, such combinations are combined with water-soluble filters such as, for example, 2-phenylbenzimidazole-5-sulphonic acid and their alkali metal, alkaline earth metal, ammonium, alkylammonium, alkanolammonium and glucammonium salts.

As well as said soluble substances, insoluble light protection pigments, namely finely dispersed metal oxides or salts, are also suitable for this purpose. Examples of suitable metal oxides are, in particular, zinc oxide and titanium dioxide and also oxides of iron, zirconium, silicon, manganese, aluminium and cerium, and mixtures thereof. Salts which may be used are silicates (talc), barium sulphate or zinc stearate. The oxides and salts are used in the form of the pigments for skincare and skin-protective emulsions and decorative cosmetics. The particles here should have an average diameter of less than 100 nm, preferably between 5 and 50 nm and in particular between 15 and 30 nm. They can have a spherical shape, but it is also possible to use particles which have an ellipsoidal shape or a shape deviating in some other way from the spherical form. The pigments can also be surface-treated, i.e. hydrophilicized or hydrophobicized. Typical examples are coated titanium dioxides, such as, for example, titanium dioxide T 805 (Degussa) or Eusolex® T2000 (Merck). Suitable hydrophobic coating agents are here primarily silicones and, specifically in this case, trialkoxyoctylsilanes or simethicones. In sunscreens, preference is given to using so-called micro- or nano-pigments. Preference is given to using micronized zinc oxide.

In one embodiment of the invention the cosmetic composition further comprises at least one biogenic active ingredient and/or antioxidant.

Biogenic active ingredients are understood as meaning, for example, tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts, such as, for example, prunus extract, bambara nut extract and vitamin complexes.

Antioxidants interrupt the photochemical reaction chain which is triggered when UV radiation penetrates the skin. Typical examples thereof are amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotenoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulphoximine compounds (e.g. buthionine sulphoximines, homocysteine sulphoximine, buthionine sulphones, penta-, hexa-, heptathionine sulphoximine) in very low tolerated doses (e.g. pmol to μmol/kg), and also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. .gamma.-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate), and coniferyl benzoate of gum benzoin, rutic acid and derivatives thereof, α-glycosylrutin, ferulic acid, furfurylideneglucitol, carnosine, butylhydroxytoluene, butylhydroxyanisole, nordihydroguaiacic acid, nordihydroguaiaretic acid, trihydroxybutyro-phenone, uric acid and derivatives thereof, mannose and derivatives thereof, superoxide dismutase, zinc and derivatives thereof (e.g. ZnO, $ZnSO_4$) selenium and derivatives thereof (e.g. selenomethionine), stilbenes and derivatives thereof (e.g., stilbene oxide, trans-stilbene oxide) and the derivatives (salts, esters, ethers, sugars, nucleotides, nucleosides, peptides and lipids) of said active ingredients which are suitable according to the invention.

In one embodiment of the invention the cosmetic composition further comprises at least one anti-microbial agent and/or preservative.

Suitable antimicrobial agents are, in principle, all substances effective against gram-positive bacteria, such as, for example, 4-hydroxybenzoic acid and its salts and esters, N-(4-chlorophenyl)-N'-(3,4-dichlorophenyl)urea, 2,4,4'-trichloro-2'-hydroxydiphenyl ether (triclosan), 4-chloro-3,5-dimethylphenol, 2,2'-methylenebis(6-bromo-4-chlorophenol), 3-methyl-4-(1-methylethyl)phenol, 2-benzyl-4-chlorophenol, 3-(4-chlorophenoxy)-1,2-propanediol, 3-iodo-2-propynyl butylcarbamate, chlorhexidine, 3,4,4'-trichlorocarbanilide (ITC), antibacterial fragrances, thymol, thyme oil, eugenol, oil of cloves, menthol, mint oil, farnesol, phenoxyethanol, glycerol monocaprate, glycerol monocaprylate, glycerol monolaurate (GML), diglycerol monocaprate (DMC), salicylic acid N-alkylamides, such as, for example, N-octylsalicylamide or N-decylsalicylamide.

Suitable preservatives are, for example, phenoxy ethanol, formaldehyde solution, parabens, pentanediol or sorbic acid, and the silver complexes known under the name Surfacins®, and also the other classes of substance listed in Annex 6, Part A and B of the Cosmetics Directive.

In one embodiment of the invention the cosmetic composition further comprises at least one film former.

Customary film formers are, for example, chitosan, microcrystalline chitosan, quaternized chitosan, polyvinylpyrrolidone, vinylpyrrolidone-vinyl acetate copolymers, polymers of the acrylic acid series, quaternary cellulose derivatives, collagen, hyaluronic acid and salts thereof, and similar compounds.

In one embodiment of the invention the cosmetic composition further comprises at least one swelling agent.

The swelling agents for aqueous phases may be montmorillonites, clay mineral substances, Pemulen, and alkyl-modified Carbopol grades (Goodrich). Other suitable polymers and swelling agents are given in the review by R. Lochhead in *Cosm. Toil.* 108, 95 (1993). In one embodiment of the invention the cosmetic composition further comprises at least one hydrotrophic agent.

To improve the flow behaviour, it is also possible to use hydrotropic agents, such as, for example, ethanol, isopropyl alcohol, or polyols. Polyols which are suitable here preferably have 2 to 15 carbon atoms and at least two hydroxyl groups. The polyols can also contain further functional groups, in particular amino groups, or be modified with nitrogen. Typical examples are glycerol; alkylene glycols, such as, for example, ethylene glycol, diethylene glycol, propylene glycol, butylene glycol, hexylene glycol, and polyethylene glycols with an average molecular weight of from 100 to 1000 daltons; technical-grade oligoglycerol mixtures with a degree of self-condensation of from 1.5 to 10, such as, for example, technical-grade diglycerol mixtures with a diglycerol content of from 40 to 50% by weight; methylol compounds, such as, in particular, trimethylolethane, trimethylolpropane, trimethylolbutane, pentaerythritol and dipentaerythritol; lower alkyl glucosides, in particular those having 1 to 8 carbon atoms in the alkyl radical, such as, for example, methyl and butyl glucoside; sugar alcohols having 5 to 12 carbon atoms, such as, for example, sorbitol or mannitol, sugars having 5 to 12 carbon atoms, such as, for example, glucose or sucrose; amino sugars, such as, for example, glucamine; dialcohol amines, such as diethanolamine or 2-amino-1,3-propanediol.

The composition may also comprise at least one binder. Among the binders that may be used, mention may be made of the magnesium stearate sold by Brenntag, the corn starch sold by Roquette, the talc sold by WCD, the cholesterol sold by Croda or the silica sold by Degussa. The binders may be used in an amount of between 0.1% and 30% by weight and preferably between 1% and 20% by weight.

Among the additives, further examples that may be mentioned include, taken alone or in combination: vitamins such as vitamin PP, vitamin C, vitamin E, or niacinamide; calmatives or anti-irritant agents such as PPG-12/SMDI copolymer sold by the company Bertek Pharmaceuticals under the trade name Polyolprepolymer-2 or glycyrrhetinic acid or derivatives thereof, for instance Enoxolone sold by Cognis; moisturizers or humectants: examples that may be mentioned include sugars and derivatives, glycols, glycerol and sorbitol; lecithins and cholesterol; preserving agents, such as the methyl paraben sold under the name Nipagin M by Clariant, the propyl paraben sold under the name Nipasol by Clariant, or the phenoxyethanol sold under the name Phenoxetol by Clariant; acids or bases such as citric acid, sodium citrate, triethanolamine, aminomethylpropanol, sodium hydroxide and diisopropanolamine; other additives for giving the said preparation specific properties.

Each of these exemplary additives, in any combination, can be present in the oily phase, the fatty phase or can be distributed amongst the phases in the formulation of the invention A subject of the invention is also the use of the composition thus obtained, as a medicament.

More particularly, the composition may be used for preparing a medicament intended for treating and preventing hyperpigmentary disorders such as melasma, chloasma, lentigo, senile lentigo, vitiligo, freckles, post-inflammatory hyperpigmentations caused by abrasion, a burn, a scar, a dermatosis or a contact allergy; naevi, genetically determined hyperpigmentations, hyperpigmentations of metabolic or medicinal origin, melanomas or any other hyperpigmentary lesions.

The compositions according to the invention also find an application in the cosmetics field, in particular in protecting against the harmful effects of sunlight, for preventing and/or combating light-induced or chronological aging of the skin and the integuments.

The invention also relates to a non-therapeutic cosmetic treatment process for beautifying the skin and/or for improving its surface appearance, characterized in that a composition comprising at least one depigmenting agent is applied to the skin and/or its integuments.

The anhydrous compositions according to the invention are obtained by a person skilled in the art using a known standard process for mixing phases.

The preparation process may include the following steps:

preparation of the active phase by incorporating the active agent into its fatty solvent, by means, if necessary, of heating;

preparation of the non-active phase(s);

incorporation of the active and non-active phases with stirring.

Methods of Treatment

Various methods of treatment, application, regulation, or improvement may utilize the aforementioned compositions. In one embodiment, the method includes the step of identifying a hyperpigmented spot for improvement by the composition. The hyperpigmented spot may be identified by the user or a third party such as a dermatologist, cosmetician, or other caregiver. Identification may be done by visual inspection of the skin for hyperpigmented spots in need of treatment based on size and/or color. Identification may also be done by commercially available imaging devices such SIAscope® V (available from Astron Clinica, Ltd., UK) or the VISIA® Complexion Analysis system (available from Canfield Scientific, Inc., Fairfield, N.J.). Both devices are capable of collecting images of the skin and identifying hyperpigmented spots. In some instances, the method comprises the step of identifying a plurality of hyperpigmented spots for treatment by the composition.

Identification of the hyperpigmented spot may occur on any skin surface of the body. Skin surfaces of the most concern tend to be those not typically covered by clothing such as facial skin surfaces, hand and arm skin surfaces, foot and leg skin surfaces, and neck and chest skin surfaces. In particular, identification of the hyperpigmented spot may be on a facial skin surface including the forehead, perioral, chin, periorbital, nose, and/or cheek skin surfaces.

The method may comprise the step of applying the composition to a hyperpigmented spot or spots, which may have been previously identified. Many regimens exist for the application of the composition to the hyperpigmented spot. The composition may be applied at least once a day, twice a day, or on a more frequent daily basis, during a treatment period. When applied twice daily, the first and second applications are separated by at least 1 to about 12 hours. Typically, the composition may be applied in the morning and/or in the evening before bed.

The treatment period is ideally of sufficient time to provide an improvement in the hyperpigmented spot. The improvement may be a detectable reduction in size of the hyperpigmented spot, whitening of the hyperpigmented spot, decrease in melanin of the hyperpigmented spot, or evening of the tone of skin. The treatment period may be at least about 1 week. The treatment period may last about 4 weeks or about 8 weeks. In certain embodiments, the treatment period will extend over multiple months (i.e., 3-12 months) or multiple years. In one embodiment the composition is applied to the hyperpigmented spot(s) at least once a day during a treatment period of at least about 4 weeks or at least about 8 weeks. In one embodiment the composition is applied to the hyperpigmented spot(s) twice a day during a treatment period of at least about 4 weeks or 8 weeks.

In still another embodiment, the method comprises applying the skin care composition according to a regimen, wherein said regimen comprises: (a) cleansing the skin to form a cleansed skin surface; (b) topically applying the composition of the invention to the cleansed skin surface. The composition of the invention may be used daily, weekly, or in a variety of regimens. The composition may be used more than once a day, such as at night and in the morning. The composition may be used more than once per day on certain days or use only a few times per week. The composition may be used three times per day, twice per day, once per day, six times per week, five times per week, four times per week, three times per week, two times per week, or one time per week. In some embodiments, the composition is used four, five, six or seven times per week.

The step of applying the composition to the hyperpigmented spot may be accomplished by localized application. In reference to application of the composition, the term "localized", "local", or "locally" mean that the composition is delivered the targeted area (such as the hyperpigmented spot) while minimizing delivery to skin surface not requiring treatment. The composition may be applied and lightly massaged into the hyperpigmented spot. It is recognized that localized application does allow for a reasonable amount of the composition to be applied to areas adjacent the hyperpigmented spot (i.e., the composition is unlikely to be applied or to remain within the boundary of the hyperpigmented spot without some spreading). The form of the composition or the dermatologically acceptable carrier should be selected to facilitate localized application. While certain embodiments of the present invention contemplate applying a composition locally to a hyperpigmented spot, it will be appreciated that compositions of the present invention can be applied more generally or broadly to one or more facial skin surfaces to reduce the appearance of hyperpigmented spots within those facial skin regions.

In some embodiments, the composition may be delivered by a variety of applicators appropriate for localized and general application. Such applicators can include droppers, applicator wands, cotton swabs, or any other suitable device. Other suitable applicators include SH-0127 pen applicator available from Shya Hsin Plastic Works, Inc., Taiwan and either the Xpress Tip or liquid filled swab available from SwabPlus, Inc., China. The applicator may be configured to easily apply the composition to hyperpigmented spots having an approximate diameter between about 2 mm and about 10 mm and allowing for a dosed amount of the composition of between about 1 to about 50 µL/cm² or between about 1 to about 5 µL/cm². In another embodiment, the composition is applied to the one or more hyperpigmented spots and more generally to one or more facial skin surfaces contemporaneously (i.e., over a period of less than 30 minutes or, more typically, less than 5 minutes).

While some methods described herein contemplate applying the compositions of the present invention with an applicator, it will be appreciated that applicators are not required and the compositions of the present invention can also be applied directly by using one's finger or in other conventional manners.

For general application to a skin surface and, particularly a facial skin surface, the dosed amount of the first or second composition may be between about 1 to about 50 µL/cm² per application (i.e., per single application to the skin surfaces).

Suitable methods may comprise any one or more of the abovementioned steps. All of the aforementioned steps are applicable to application, treatment, regulation, and/or improvement of both a single hyperpigmented spot as well as a plurality of hyperpigmented spots. Likewise, the exemplary methods that follow are applicable to both a single hyperpigmented spot as well as a plurality of hyperpigmented spots.

One suitable method of improving the appearance of a hyperpigmented spot includes the step of topically applying a composition of the invention comprising an effective amount of a compound according to Formula I to the hyperpigmented spot on a skin surface, wherein the composition is applied for a period of time sufficient to improve the appearance of the hyperpigmented spot. Another suitable method of improving the appearance of hyperpigmented spots includes the steps of identifying a hyperpigmented spot on a skin surface, applying a composition comprising an effective amount of a compound according to Formula I, wherein the composition is applied for a period of time sufficient to improve the appearance of the hyperpigmented spot.

Another suitable method is for improving the appearance of a post-inflammatory hypopigmentation. The method may comprise the steps of identifying an area of post-inflammatory hypopigmentation on a skin surface and of applying to the area a composition of the invention, which also provides anti-inflammatory effect. An effective amount of said composition may be applied at least daily for a period of time sufficient to improve the appearance of the area of post-inflammatory hypopigmentation. The skin care compositions may further comprise a sunscreen active, an additional skin tone agent, or combinations thereof.

The formulation examples below illustrate exemplary compositions according to the invention without, however, limiting the scope thereof. The amounts of the constituents are expressed as weight percentages relative to the total weight of the composition.

EXAMPLES

For the measurement of the flow threshold, a VT550 Haake rheometer with an SVDIN measuring spindle was used.

The rheograms are produced at 25° C. at an imposed speed of 0 to 100 s$^{-1}$. The viscosity values are given at shear values of 4 s$^{-1}$, 20 s$^{-1}$, 100 s$^{-1}$($\gamma$). The term "flow threshold" ($\tau_0$ expressed in Pascals) means the force (minimum shear stress) required to overcome the cohesion forces of van der Waals type and to bring about flow.

Example 1

| Formulation | |
|---|---|
| Ingredients | Weight % |
| Isododecane | 10% |
| PPG-14 Butyl Ether | 10% |
| Caprylic/Capric Triglyceride | 10% |
| Isononyl Isononanoate | 8% |
| Benzyl Alcohol | 0.5% |
| Tocopheryl Acetate | 0.05% |
| BHT | 0.2% |
| Tetrahydropyranyloxy Phenol | 6% |
| Ethanol | 2-4% |
| Caprylyl Methicone | 7% |
| PEG-10 dimethicone | 10% |
| Cyclopentasiloxane | 38-40% |

| | | | STABILITY | | | |
|---|---|---|---|---|---|---|
| Property | Specification | 1 Week | 1 Month | 2 Months | 3 Months | 6 Months |
| | | | INCUBATED AT 25° C. | | | |
| Color | Colorless - Beige | Colorless | Colorless | Colorless | Colorless | Colorless |
| Odor | Characteristic | Odorless | Odorless | Odorless | Odorless | Odorless |
| Appearance | Clear Liquid | Clear Liquid | Clear Liquid | Clear Liquid | Clear Liquid | Clear Liquid |
| Tetrahydropyranyloxy phenol | 5.6-6.6% | 6.60% | 5.80% | 6.50% | 5.80% | 5.70% |
| Hydroquinone | <0.002% | Non detectable | Non detectable | Non detectable | Non detectable | Non detectable |
| | | | INCUBATED AT 40° C. | | | |
| Color | Colorless - Beige | Colorless | Colorless | Colorless | Beige | Beige |

-continued

| | STABILITY | | | | | |
|---|---|---|---|---|---|---|
| Property | Specification | 1 Week | 1 Month | 2 Months | 3 Months | 6 Months |
| Odor | Characteristic | Odorless | Odorless | Odorless | Odorless | Odorless |
| Appearance | Clear Liquid | Clear Liquid | Clear Liquid | Clear Liquid | Clear Liquid | Clear Liquid |
| Tetrahydro-pyranyloxy phenol | 5.0-7.0% | 6.50% | 5.60% | 6.30% | 5.80% | 5.80% |
| Hydroquinone | <0.002% | Non detectable | Non detectable | Non detectable | Non detectable | Non detectable |

Procedure:

1. Solution A: To a 250 mL round bottom flask with a mechanical stirring was charged with 10 g of isododecane, 10 g of PPG-14 butyl ether, 10 g of caprylic/capric triglyceride, 8 g of isononyl isononanoate, 0.5 g of benzyl alcohol, and 0.05 g of tocopheryl acetate. The mixture was stirred at room temperature for 20 min, resulting in a clear solution.

2. Solution B: To a 25 mL round bottom flask with magnetic stirring was charged with 0.2 g of BHT, 6 g of (4-tetrahydro-pyran-2-yloxy)-phenoland 6 g of ethanol. The mixture was stirred at room temperature for 1 h, resulting in a clear solution.

3. Solution B was added to Solution A to get Solution C. Mixture C was stirred for 20 min. Then most of the ethanol was removed via rotary evaporation under reduced pressure.

4. To Solution C was added 7 g of caprylyl methicone, 10 g of PEG-10 dimethicone and 39 g of cyclopentasiloxane. The mixture was stirred for 30 min, resulting in a colorless and transparent formula.

Example 2

| Formulation | |
|---|---|
| Ingredients | Weight % |
| Isododecane | 8% |
| PPG-14 Butyl Ether | 8% |
| Caprylic/Capric Triglyceride | 10% |
| Isononyl Isononanoate | 8% |
| Benzyl Alcohol | 0.5% |
| Tocopheryl Acetate | 0.05% |
| BHT | 0.2% |
| Tetrahydropyranyloxy Phenol | 6% |
| Isopropyl alcohol | 6% |
| Caprylyl Methicone | 7% |
| PEG-10 dimethicone | 10% |
| Cyclopentasiloxane | 36% |

Procedure:

1. Solution A: To a 500 mL round bottom flask with a mechanical stirring was charged with 40 g of isododecane, 50 g of PPG-14 butyl ether, 50 g of caprylic/capric triglyceride, 40 g of isononyl isononanoate, 2.5 g of benzyl alcohol and 0.25 g of tocopheryl acetate. The mixture was stirred at room temperature for 20 min, resulting in a clear solution.

2. Solution B: To a 100 mL round bottom flask with a mechanical stirring was charged with 1 g of BHT, 30 g of (4-tetrahydro-pyran-2-yloxy)-phenoland 30 g of isopropyl alcohol. The mixture was stirred at room temperature for 1 h, resulting in a clear and colorless solution.

3. Solution B was added to Solution A to get Solution C. Mixture C was stirred for 20 min.

4. To Solution C was added 35 g of caprylyl methicone, 50 g of PEG-10 dimethicone and 180 g of cyclopentasiloxane. The mixture was stirred for 30 min, resulting in a colorless formula.

Example 3

| Formulation | |
|---|---|
| Ingredients | Weight % |
| PPG-14 Butyl Ether | 20% |
| Caprylic/Capric Triglyceride | 10% |
| Isononyl Isononanoate | 10% |
| Caprylyl Methicone | 8% |
| Cyclomethicone | 40% |
| BHT | 0.2% |
| Tetrahydropyranyloxy Phenol | 10% |
| Ethanol | 2% |

| | | Stability Incubated at 70° C. | | | | | | | |
|---|---|---|---|---|---|---|---|---|---|
| Property | Specification | 1 DAY | 5 DAYS | 7 DAYS | 9 DAYS | 12 DAYS | 14 DAYS | 18 DAYS | 26 DAYS |
| Color | Colorless - Beige | Colorless | Beige | Beige | Beige | Beige | Beige | Beige | Beige |
| Odor | Characteristic | Odorless | Odorless | Odorless | Odorless | Odorless | Odorless | Odorless | Odorless |
| Appearance | Clear Liquid | Clear Liquid | Clear Liquid | Clear Liquid | Clear Liquid | Clear Liquid | Clear Liquid | Clear Liquid | Clear Liquid |
| Tetrahydro-pyranyloxy phenol | 6.16% | 6.14% | 6.08% | 6.16% | 6.06% | 6.19% | 6.00% | 6.20% | 6.1% |
| Hydroquinone | <0.002% | Non detectable | Non detectable | Non detectable | Non detectable | 0.004% | 0.004% | 0.004% | 0.008% |

| STABILITY | | | | |
|---|---|---|---|---|
| TEMPERATURES | PROPERTIES | SPECIFICATION | 7 DAYS | 2 MONTHS |
| INCUBATED AT 25° C. | COLOR | Colorless - Beige | Colorless | Colorless |
| | ODOR | Characteristic | Odorless | Odorless |
| | APPEARANCE | Clear Liquid | Clear Liquid | Clear Liquid |
| | Hydroquinone | <0.002% | Non detectable | Non detectable |
| INCUBATED AT 40° C. | COLOR | Colorless - Beige | Colorless | Colorless |
| | ODOR | Characteristic | Odorless | Odorless |
| | APPEARANCE | Clear Liquid | Clear Liquid id | Clear Liquid |
| | Hydroquinone | <0.002% | Non detectable | Non detectable |

Procedure

1. Solution A: To a 50 mL round bottom flask with magnetic stirring was charged with 5 g of PPG-14 butyl ether, 2.5 g of caprylic/capric triglyceride, 2.5 g of isononyl isononanoate and 2 g of caprylyl methicone. The mixture was stirred at room temperature for 20 min, resulting in a clear and colorless solution.

2. Solution B: To a 20 mL glass bottle with magnetic stirring was charged with 0.05 g of BHT, 2.5 g of (4-tetrahydro-pyran-2-yloxy)-phenol, 3 g of ethanol and 1 drop of triethanolamine. The mixture was stirred at room temperature for 1 h, resulting in a clear and colorless solution.

3. Solution B was added to Solution A to produce Solution C. The mixture was stirred for 20 min. Then most of ethanol was removed using rotary evaporator under reduced pressure.

4. To Solution C was added 10 g of cyclomethicone. The mixture was stirred for 30 min to result a colorless and transparent formula.

Example 4

| Formulation | |
|---|---|
| Ingredients | Weight % |
| Caprylic/Capric Triglyceride | 8% |
| Isononyl Isononanoate | 5% |
| Isopropyl Palmitate | 5% |
| Light Mineral Oil | 5% |
| Tocopheryl Acetate | 2% |
| Cetostearyl Alcohol | 10% |
| BHT | 0.7% |
| Benzyl Alcohol | 0.5% |
| Polyisobutene | 34% |
| Elsker Baby Oil | 10% |
| Tetrahydropyranyloxy Phenol | 10% |
| Ethanol | 10% |

Procedure

1. Solution A: To a 25 mL round bottom flask with magnetic stirring was charged with 1.6 g of caprylic/capric Triglyceride, 1 g of Isononyl Isononanoat, 1 g of isopropyl palmitate, and 1 g of Light Mineral Oil, 0.4 g of tocopheryl acetate, 2 g of cetostearyl alcohol, 0.14 g of BHT, 0.1 g of benzyl alcohol, 6 g of polyisobutene and 2 g of Elsker Baby Oil. The mixture was warmed to 70° C. and stirred for 20 min, resulting in a clear and colorless solution, then cooled to 30° C.

2. Solution B: To a 25 mL round bottom flask with magnetic stirring was charged with 2 g of (4-tetrahydro-pyran-2-yloxy)-phenol and 2 g of ethanol. The mixture was stirred at room temperature for 30 min, resulting in a colorless and transparent solution.

3. Solution B was added to Solution A to get Solution C. Mixture C was stirred for 20 min, resulting in a colorless and transparent formula.

Example 5

| Formulation | |
|---|---|
| Ingredients | Weight % |
| Elsker Baby Oil | 87% |
| BHT | 0.6% |
| Tetrahydropyranyloxy Phenol | 6.2% |
| Ethanol | 6.2% |

| STABILITY | | | | |
|---|---|---|---|---|
| TEMPERATURES | PROPERTIES | SPECIFICATION | 2 DAYS | 7 DAYS |
| INCUBATED AT 25° C. | COLOR | Colorless - Beige | Colorless | Colorless |
| | ODOR | Characteristic | Odorless | Odorless |
| | APPEARANCE | Clear Liquid | Clear Liquid | Clear Liquid |
| | Hydroquinone | <0.002% | Non detectable | Non detectable |
| INCUBATED AT 40° C. | COLOR | Colorless - Beige | Colorless | Colorless |
| | ODOR | Characteristic | Odorless | Odorless |
| | APPEARANCE | Clear Liquid | Clear Liquid | Clear Liquid |
| | Hydroquinone | <0.002% | Undetected | Undetected |

| STABILITY | | | | |
|---|---|---|---|---|
| TEMPERATURES | PROPERTIES | SPECIFICATION | 3 DAYS | 7 DAYS |
| INCUBATED AT 25° C. | COLOR | Colorless - Beige | Colorless | Colorless |
| | ODOR | Characteristic | Odorless | Odorless |
| | APPEARANCE | Clear Liquid | Clear Liquid | Clear Liquid |
| | Hydroquinone | <0.002% | Non detectable | Non detectable |
| INCUBATED AT 40° C. | COLOR | Colorless - Beige | Colorless | Colorless |
| | ODOR | Characteristic | Odorless | Odorless |
| | APPEARANCE | Clear Liquid | Clear Liquid | Clear Liquid |
| | Hydroquinone | <0.002% | Non detectable | Non detectable |

Procedure

1. Solution A: To a 25 mL round bottom flask with magnetic stirring was charged with 8.4 g of Elsker Baby Oil and 0.06 g of BHT. The mixture was stirred at room temperature for 40 min, resulting in a clear, colorless and transparent solution.

2. Solution B: To a 25 mL round bottom flask with magnetic stirring was charged 0.6 g of (4-tetrahydro-pyran-2-yloxy)-phenol and 0.6 g of ethanol. The mixture was stirred at room temperature for 30 min, resulting in a clear, colorless and transparent solution.

3. Solution B was added to Solution A to get Solution C. Mixture C was stirred for 20 min, resulting in a colorless and transparent formula.

Example 6

| Formulation | |
|---|---|
| Ingredients | Weight % |
| Versagel M750 | 64.50% |
| Isopropyl Isostearate | 3% |
| Caprylic/Capric Triglyceride | 5% |
| Isopropyl Palmitate | 8% |
| Isohexadecane | 7% |
| Benzyl Alcohol | 0.3% |
| BHT | 0.2% |
| Tetrahydropyranyloxy Phenol | 10.% |
| Ethanol | 1~2% |
| Triethanolamine | 3 drops |

Procedure

1. Gel mixture A: To a 1 L reactor with a mechanical stirring and nitrogen protection was charged with 129 g of Versagel M750, 6 g of isopropyl isostearate, and 10 g of caprylic/capric triglyceride, and 16 g of isopropyl palmitate, and 14 g of isohexadecane and 0.6 g of benzyl alcohol. The mixture was warmed to and stirred at 80° C. for 40 min, resulting in a colorless and transparent gel, then cooled to 30° C.

2. Solution B: To a 100 mL round bottom flask with a mechanical stirring was charged 0.4 g of BHT, 20 g of (4-tetrahydro-pyran-2-yloxy)-phenol and 24 g of ethanol and 3 drops of triethanolamine. The mixture was stirred at room temperature for 30 min, resulting in a clear and colorless solution.

3. Solution B was added to Gel A to produce Gel C. Mixture C was stirred for 30 min, following which most of the ethanol was removed using rotary evaporator under reduced pressure resulting in a milky gel.

Example 7

| Formulation | |
|---|---|
| Ingredients | Weight % |
| Water (Aqua) | 43.75% |
| Acrylates/C10-30 Alkyl Acrylate Crosspolymer | 0.19% |
| Disodium EDTA | 0.05% |
| Chlorphenesin | 0.25% |
| Butylene Glycol | 1.25% |
| Tocopheryl Acetate | 0.06% |
| PPG-14 Butyl Ether | 6.25% |
| Cetyl Alcohol | 2.75% |
| Stearyl Alcohol | 1.5% |
| BHT | 0.28% |
| Steareth-21 | 1.88% |
| Steareth-2 | 1.% |
| Tetrahydropyranyloxy Phenol | 5.5% |
| Ethanol | 5.5% |
| β-Cyclodextrin | 25% |
| Sodium Metabisulfite | 0.25% |

| STABILITY | | | | | |
|---|---|---|---|---|---|
| TEMPERATURE | PROPERTIES | SPECIFICATION | 19 DAYS | 40 DAYS | 60 DAYS |
| INCUBATED AT 25° C. | COLOR | White - Beige | White | White | White |
| | ODOR | Characteristic | Odorless | Odorless | Odorless |
| | APPEARANCE | Clear Gel | Clear Gel | Clear Gel | Clear Gel |
| | Hydroquinone | <0.002% | Non detectable | Non detectable | Non detectable |
| INCUBATED AT 40° C. | COLOR | Colorless - Beige | Milky | Milky | Milky |
| | ODOR | Characteristic | Odorless | Odorless | Odorless |
| | APPEARANCE | Clear Gel | Clear Gel | Clear Gel | Clear Gel |
| | Hydroquinone | <0.002% | Non detectable | Non detectable | Non detectable |

-continued

| Formulation | |
|---|---|
| Ingredients | Weight % |
| Magnesium Ascorbyl Phosphate | 0.18% |
| Polyaminopropyl Biguanide | 0.88% |

-continued

| Formulation | |
|---|---|
| Ingredients | Weight % |
| Dimethicone | 1.75% |
| Benzyl Alcohol | 0.88% |
| Lactic Acid | drops |
| Triethanolamine | drops |

| STABILITY (incubated at 40° C.) | | | | | | |
|---|---|---|---|---|---|---|
| PROPERTIES | SPECIFICATION | 10 DAYS | 17 DAYS | 21 DAYS | 30 DAYS | 45 DAYS |
| COLOR | White - Beige | White (Red in the bottom) | White (Red in the bottom) | White (Red in the bottom) | White (Red in the bottom) | White (Red in the bottom) |
| ODOR | Characteristic | Odorless | Odorless | Odorless | Odorless | Odorless |
| APPEARANCE | Cream | Cream | Cream | Cream | Cream | Cream |
| Hydroquinone | <0.002% | Non detectable | Non detectable | Non detectable | Non detectable | 0.002% |

Procedure

1. Mixture A: To a 50 mL three-neck flask with a mechanical stirring and nitrogen protection was charged with 20 g of water, 4.4 g of (4-tetrahydro-pyran-2-yloxy)-phenol, 4.4 g of ethanol and 20 g of β-CD. The mixture was stirred overnight at room temperature. The pH value was adjusted to 8.8 with lactic acid and triethanolamine.

2. Mixture B: A 250 mL three-neck flask with a mechanical stirrer and under nitrogen protection was charged 15 g of water and 0.15 g of acrylates/$C_{10-30}$ alkyl acrylate crosspolymer. The mixture was warmed to and stirred for 20 min at 75° C. Then 0.04 g of disodium EDTA, 0.2 g of chlorphenesin and 1 g of butylene glycol were added to the mixture one by one and the resulting mixture was well stirred.

3. Mixture C: To a 50 mL three-neck flask with a mechanical stirring and nitrogen protection was charged 0.05 g of tocopheryl acetate, 5 g of PPG-14 Butyl Ether, 2.2 g of cetyl alcohol, 1.2 g of stearyl alcohol, 0.22 g of BHT, 1.5 g of Steareth-21 and 0.8 g of Steareth-2. The mixture was warmed to 75° C. and stirred for 30 min dissolving the components.

4. Mixture C was added to Mixture B under heating, resulting in Mixture D. Mixture D was stirred for 30 min and cooled to 60° C. After the pH of the mixture was adjusted to 7.98 with Triethanolamine, the mixture was cooled to 55° C.

5. Mixture A was heated to 55° C. and added to Mixture D, and the resulting mixture was well stirred before it was cooled to 45° C. To the mixture, 0.2 g of sodium metabisulfite, 0.14 g of magnesium ascorbyl phosphate, 0.7 g of polyaminopropyl biguanide and 1.4 g of Dimethicone were added. The resulting mixture was stirred for 40 min, then cooled to 35° C. After 0.7 g of benzyl alcohol was added, the mixture was stirred for 30 min and cooled to 30° C., resulting in a milky viscous cream.

6. The formula was put into a glass bottle and store at 4° C. under nitrogen protection.

Example 8

| Formulation | |
|---|---|
| Ingredients | Weight % |
| Polyisobutene (H300) | 9 |
| Isododecane | 23 |
| cyclopentasiloxane | 32 |
| PPG-14 Butyl Ether | 7 |
| Caprylic/Caprictriglyceride | 10 |
| Benzyl Alcohol | 0.5 |
| Tocopheryl Acetate | 0.05 |
| Caprylyl Methicone | 7 |
| Silica Dimethyl Silylate | 3 |
| Cetyl Alcohol | 1 |
| Stearyl Alcohol | 1 |
| Triethanolamine | 0.15 |
| BHT | 0.2 |
| Tetrahydropyranyloxy Phenol | 6 |

| Stability (incubated at 40 °C.) | | | | | | |
|---|---|---|---|---|---|---|
| PROPERTIES | SPECIFICATION | 0 DAY | 1 WEEK | 1 MONTH | 2 MONTHS | 3 MONTHS |
| Apperance | Liquid | Liquid | Liquid | Liquid | Liquid | Liquid |
| Color | White - Beige | White | White | White | White | White |
| Hydroquinone | <0.002% | Non detectable | Non detectable | Non detectable | Non detectable | Non detectable |

Procedure

1. To a solution of 69.00 g of Isododecane in a 500 mL reactor with a mechanical stirring and under a blank of nitrogen gas was added 27.00 g of polyisobutene (H300) at room temperature. The mixture was stirred to become a clear liquid and 21 g of PPG-14 butyl ether, 30 g of caprylic/caprictriglyceride, 1.5 g of benzyl alcohol, 0.15 g of tocopheryl acetate, 21 g of caprylyl methicone and 9 g of fumed silica were added respectively to the mixture. The mixture was stirred at room temperature for 5 min and homogenized to become a clear liquid under a blank of nitrogen gas at room temperature.

2. 3 g of cetyl alcohol, 3 g of stearyl alcohol, 0.6 g of BHT were added to phase A, respectively. The resulting mixture was heated to 70° C. until homogeneous and cooled to room temperature under a blanket of nitrogen. 96 g of cyclopentasiloxane and 0.45 g of triethanolamine were added to the mixture and the mixture was stirred to give a colorless liquid.

3. Micronized tetrahydropyranyloxy phenol was added to Phase B under nitrogen atmosphere. The mixture was stirred and homogenized to give the final product as a milky liquid. The pH of the final product was confirmed to be between pH=7.8-8.0 and adjusted as needed with triethanolamine or lactic acid.

Example 9

| Formulation | |
|---|---|
| Ingredients | Weight % |
| Water (Aqua) | 64.9% |
| Acrylates/$C_{10-30}$ Alkyl Acrylate Crosspolymer | 0.2% |
| Disodium EDTA | 0.05% |
| Chlorphenesin | 0.27% |
| Butylene Glycol | 1.36% |
| Tocopheryl Acetate | 0.07% |
| PPG-14 Butyl Ether | 6.83% |
| Cetyl Alcohol | 3.00% |
| Stearyl Alcohol | 1.64% |
| BHT | 0.22% |
| Steareth-21 | 2.00% |
| Steareth-2 | 1.10% |
| Tetrahydropyranyloxy Phenol | 6.00% |
| β-Cyclodextrin | 10.20% |
| Sodium Metabisulfite | 0.16% |
| Magnesium Ascorbyl Phosphate | 0.11% |
| Polyaminopropyl Biguanide | 0.55% |
| Dimethicone | 1.00% |
| Benzyl Alcohol | 0.27% |
| Lactic Acid | drops |
| Triethanolamine | drops |

| Stability (incubated at 40° C.) | | | | | |
|---|---|---|---|---|---|
| Items | Specifications | 7 DAYS | 14 DAYS | 17 DAYS | 30 DAYS |
| Apperance | Viscous Cream | Viscous Cream | Viscous Cream | Viscous Cream | Viscous Cream |
| Color | White - Beige | White | White | White | Beige |
| Hydroquinone | <0.002% | Non detectable | Non detectable | Non detectable | Non detectable |

Procedure

1. Mixture A: To a 50 mL three-neck flask with a mechanical stirring and nitrogen protection was charged 20 g of water and 12.5 g of β-cyclodextrin. The mixture was stirred and the pH value was adjusted to 8.56 with lactic acid and triethanolamine. To the mixture, 4.4 g of tetrahydropyranyloxyphenol was added and the resulting mixture was stirred overnight at room temperature.

2. Mixture B: A 250 mL three-neck flask with a mechanical stirrer and under nitrogen protection was charged 22.5 g of water and 0.15 g of acrylates/$C_{10-30}$ alkyl acrylate crosspolymer. The mixture was warmed to 75° C. and stirred for 20 min. To the mixture, 0.04 g of disodium EDTA, 0.2 g of chlorphenesin, and 1 g of butylene glycol were added one by one and the mixture was well stirred.

3. Mixture C: To a 50 mL three-neck flask with a mechanical stirring and nitrogen protection was charged 0.05 g of tocopheryl acetate, 5 g of PPG-14 butyl ether, 2.2 g of cetyl alcohol, 1.2 g of stearyl alcohol, 0.16 g of BHT, 1.5 g of Steareth-21 and 0.8 g of Steareth-2. The mixture was warmed to 75° C. and stirred for 30 min until the components were dissolved.

4. Mixture C was added to Mixture B under heating to produce Mixture D. Mixture D was stirred for 30 min before being cooled to 60° C. The pH of the mixture was adjusted to 7.73 with triethanolamine before being cooled to 55° C.

5. Mixture A was heated to 55° C. and added to Mixture D with stirring before being cooled to 45° C. To the mixture, 0.12 g of sodium metabisulfite, 0.08 g of magnesium ascorbyl phosphate, 0.4 g of polyaminopropyl biguanide and 0.7 g of dimethicone were added. The mixture was stirred for 40 min at 55° C. before being cooled to 35° C. To the above mixture, 0.2 g of benzyl alcohol was added and the resulting mixture was stirred for 30 min. After the mixture was cooled to 30° C., the pH of the mixture was adjusted to 7.98 with triethanolamine, resulting in a milky viscous cream.

6. The formula was transferred into a glass bottle and stored at 4° C. under nitrogen protection.

Example 10

| Formulation | |
|---|---|
| Ingredients | Weight % |
| Transgel 110 | 61.5% |
| Isopropyl Isostearate | 4% |
| Dimethicone | 4% |
| Benzyl Alcohol | 0.3% |
| BHT | 0.2% |
| Tetrahydropyranyloxy Phenol | 6.% |
| Ethanol | ~2% |
| Cyclopentasiloxane | 22% |

| Stability | | | | | | | |
|---|---|---|---|---|---|---|---|
| | | 7 Days | | 30 Days | | 60 Days | |
| Items | Specifications | 25° C. | 40° C. | 25° C. | 40° C. | 25° C. | 40° C. |
| Apperance | Gel | Gel | Gel | Gel | Gel | Gel | Gel |
| Color | Milky white | Milky white | Milky white | Milky white | Milky white | Milky white | Milky white |
| Hydroquinone | <0.002% (20 ppm) | ND | 294 ppm | 43.6 ppm | 2416 ppm | 129 ppm | 6900 ppm |

Procedure

1. Solution A: A 1 L vacuum reactor with a mechanical stirrer was charged with 184.5 g of Transgel 110, 12 g of isopropyl isostearate, 12 g of Dimethicone and 0.9 g of benzyl alcohol. The mixture was heated up to 80° C. and stirred at 80° C. for 1 h under nitrogen protection, producing a milky white gel before cooled to 30° C.

2. Solution B: A 100 mL round bottom flask with a mechanical stirring was charged 0.6 g of BHT, 18 g of tetrahydropyranyloxy phenol, and 22 g of ethanol. The mixture was stirred at room temperature for 30 min, resulting in a clear colorless solution.

3. Solution B was added to Solution A at 30° C. and stirred for 20 min. Ethanol was removed under reduced pressure using a vacuum pump to produce a milky white gel. To the milky white gel was added cyclopentasiloxane. The resulting mixture was stirred vigorously to form a milky white gel.

Example 11

| Formulation | |
|---|---|
| Ingredients | Weight % |
| Transgel 110 | 64.48% |
| Isopropyl Isostearate | 3% |
| Caprylic/Capric Triglyceride | 12% |
| Benzyl Alcohol | 0.3% |
| BHT | 0.2% |
| Tetrahydropyranyloxy Phenol | 10% |
| Ethanol | 10% |

| Stability (incubated at 40° C.) | | | | |
|---|---|---|---|---|
| Items | Specifications | 7 DAYS | 20 DAYS | 60 DAYS |
| Apperance | Gel | Gel | Gel | Gel |
| Color | Milky white | Milky white | Milky white | Milky white |
| HQ | <0.002% (20 ppm) | 37 ppm, | 90 ppm, | 470 ppm |

Procedure

1. Solution A: To a 100 mL round bottom flask with a mechanical stirring was charged 32.24 g of Transgel 110, 1.5 g of isopropyl isostearate, 6 g of caprylic/capric triglyceride, and 0.5 g of benzyl alcohol. The mixture was heated up to 90° C. and stirred at 90° C. for 1 h to get a milky white gel before cooled to 40° C.

2. Solution B: To a 25 mL round bottom flask with a magnetic stirring was charged 0.1 g of BHT, 5 g of tetrahydropyranyloxy phenol, and 5 g of ethanol. The mixture was stirred at room temperature for 30 min to get a clear colorless viscous solution.

3. Solution B was added to Solution A at 40° C. and stirred at 40° C. for 20 min to produce an opaque gel before being cooled to room temperature.

4. The formula was transferred into a glass bottle and stored at 4° C. under nitrogen protection.

Example 12

| Formulation | |
|---|---|
| Ingredients | Weight % |
| Polyisobutene (H300) | 10% |
| Isododecane | 24% |
| Cyclopentasiloxane | 24% |
| PPG-14 Butyl Ether | 7.3% |
| Caprylic/Caprictriglyceride | 10% |
| Benzyl Alcohol | 0.5% |
| Tocopheryl Acetate | 0.05% |
| Caprylyl Methicone | 7% |
| Silica Dimethyl Silylate | 3% |
| BHT | 0.2% |
| Tetrahydropyranyloxy Phenol | 6% |
| Isopropyl Alcohol | 8% |
| Perfume | 0.2% |

Procedure

1. Phase A

To a solution of 24.00 g of isododecane in a 250 mL round bottom flask with mechanical stirring and under a blanket of nitrogen gas was added 10.00 g of polyisobutene (H300) at room temperature. The mixture was stirred to become a clear liquid.

2. Phase B

To Phase A, 24.00 g of cyclopentasiloxane, 7.30 g of PPG-14 butyl ether, 10.00 g of caprylic/caprictriglyceride, 0.50 g of benzyl alcohol, 0.05 g of tocopheryl acetate, and 7.00 g of caprylyl methicone were added. The resulting mixture was stirred to become a clear liquid under a blanket of nitrogen gas at room temperature.

3. Phase C

To Phase B, 3.00 g of fumed silica was added. The resulting mixture was stirred and homogenized to become a clear liquid under a blanket of nitrogen at room temperature.

4. Phase D

To a separate 50 mL round bottom flask with a mechanical stirrer and under a blanket of nitrogen was added 0.2 g of BHT, 6.00 g of tetrahydropyranyloxy phenol, 8.00 g of isopropyl alcohol, and 0.2 g of perfume. The mixture was stirred until it became a clear solution.

5. Phase E

Phase D was added to Phase C under a blanket of nitrogen gas. The mixture was stirred to give the final product as a clear liquid.

6. Phase F

The product was filled into a bottle under a blanket of nitrogen.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An anhydrous cosmetic or pharmaceutical dermatological formulation for use in depigmenting skin or otherwise lightening the tone of skin to which it is applied, said formulation comprising an active depigmenting agent which is deoxyarbutin;

a fatty phase in which the active depigmenting agent is not soluble; and less than 20% by weight relative to the total weight of the formulation of an oily phase in which the active depigmenting agent is dissolved, said oily phase consisting of ethanol and/or isopropanol;

wherein said formulation contains 0.1% or less water by weight relative to the total weight of the formulation; and wherein after storage of said formulation at 40° C. for 60 days, said formulation contains less than 20 ppm hydroquinone, either added or produced by degradation of deoxyarbutin to hydroquinone.

2. The formulation according to claim 1, wherein said fatty phase is a dermatologically acceptable carrier and said oily phase is incorporated into said dermatologically acceptable carrier.

3. The formulation according to claim 1, wherein said fatty phase is a dermatologically acceptable carrier, said oily phase is incorporated into said dermatologically acceptable carrier, and said dermatologically acceptable carrier comprises an organosilicon compound.

4. The formulation according to claim 2, wherein the dermatologically acceptable carrier is a gel, paste, serum, or cream.

5. The formulation according to claim 3, wherein the dermatologically acceptable carrier is a gel, paste, serum, or cream.

6. The formulation according to claim 1, wherein said formulation contains no more than 0.01% water by weight relative to the total weight of the formulation.

7. A method of lightening or depigmenting the skin of a subject, comprising topically applying to skin of a subject in need of such treatment a therapeutically effective amount of the formulation according to claim 1.

8. An anhydrous cosmetic or pharmaceutical dermatological formulation for use in depigmenting skin or otherwise lightening the tone of skin to which it is applied, said formulation comprising an active depigmenting agent which is deoxyarbutin;

a fatty phase in which the active depigmenting agent is not soluble; and less than 20% by weight relative to the total weight of the formulation of an oily phase in which the active depigmenting agent is dissolved;

wherein said formulation contains 0.1% or less water by weight relative to the total weight of the formulation;

wherein deoxyarbutin is the only active depigmenting agent in said formulation; and wherein after storage of said formulation at 40° C. for 60 days, said formulation contains less than 20 ppm hydroquinone, either added or produced by degradation of deoxyarbutin to hydroquinone.

9. The formulation according to claim 8, wherein said formulation contains no more than 0.01% water by weight relative to the total weight of the formulation.

10. The formulation according to claim 8, wherein said oily phase is an alcohol oily phase.

11. The formulation according to claim 10, wherein said fatty phase is a dermatologically acceptable carrier, said oily phase is incorporated into said dermatologically acceptable carrier, and said dermatologically acceptable carrier comprises an organosilicon compound.

12. The formulation according to claim 11, wherein said dermatologically acceptable carrier is a gel, paste, serum, or cream.

13. The formulation according to claim 8, wherein said oily phase is an alcohol oily phase, said fatty phase is a dermatologically acceptable carrier, and said alcohol oily phase is incorporated into said dermatologically acceptable carrier.

14. The formulation according to claim 13, wherein said dermatologically acceptable carrier is a gel, paste, serum, or cream.

15. The formulation according to claim 8, wherein said oily phase is an alcohol oily phase, said fatty phase is a dermatologically acceptable carrier, said alcohol oily phase is incorporated into a dermatologically acceptable carrier, and said dermatologically acceptable carrier comprises an organosilicon compound.

16. The formulation according to claim 15, wherein said dermatologically acceptable carrier is a gel, paste, serum, or cream.

17. A method of lightening or depigmenting the skin of a subject, comprising topically applying to skin of a subject in need of such treatment a therapeutically effective amount of the formulation according to claim 8.

18. An anhydrous cosmetic or pharmaceutical dermatological formulation for use in depigmenting skin or otherwise lightening the tone of skin to which it is applied, said formulation comprising an active depigmenting agent which is deoxyarbutin; and a fatty phase in which the active depigmenting agent is not soluble, wherein the active depigmenting agent is suspended as a particulate solid consisting of said active depigmenting agent;

wherein said formulation contains 0.1% or less water by weight relative to the total weight of the formulation; and wherein after storage of said formulation at 40° C. for 60 days, said formulation contains less than 20 ppm hydroquinone, either added or produced by degradation of deoxyarbutin to hydroquinone.

19. The formulation according to claim 18, wherein said formulation contains no more than 0.01% water by weight relative to the total weight of the formulation.

20. The formulation according to claim 18, wherein said fatty phase is a dermatologically acceptable carrier or is incorporated into a dermatologically acceptable carrier.

21. The formulation according to claim 20, wherein said dermatologically acceptable carrier comprises an organosilicon compound.

22. The formulation according to claim 20, wherein said dermatologically acceptable carrier is a gel, paste, serum, or cream.

23. The formulation according to claim 18, wherein said particulate solid has a particle size of from about 0.01 µm to about 1000 µm in diameter.

24. The formulation according to claim 23, wherein said particulate solid has a particle size of torn about 0.1 µm to about 100 µm in diameter.

25. The formulation according to claim 24, wherein said particulate solid has a particle size of from about 0.2 µm to about 50 µm in diameter.

26. The formulation according to claim 18, wherein deoxyarbutin is the only active depigmenting agent in said formulation.

27. A method of lightening or depigmenting the skin of a subject, comprising topically applying to skin of a subject in need of such treatment a therapeutically effective amount of the formulation according to claim 18.

* * * * *

UNITED STATES PATENT AND TRADEMARK OFFICE
CERTIFICATE OF CORRECTION

| | | |
|---|---|---|
| PATENT NO. | : 9,687,433 B2 | Page 1 of 1 |
| APPLICATION NO. | : 14/879704 | |
| DATED | : June 27, 2017 | |
| INVENTOR(S) | : Wang et al. | |

It is certified that error appears in the above-identified patent and that said Letters Patent is hereby corrected as shown below:

In the Specification

Column 7, Line 67: Please correct "R', R", R'" and R''''" to read -- R', R", R'" and R"" --

Column 8, Line 28: Please correct "-NR-C(NR'R"R''')=NR''''" to read -- -NR-C(NR'R"R''')=NR"" --

Column 8, Line 28: Please correct "-S(Q)R'" to read -- -S(O)R' --

Column 8, Line 48: Please correct "-A-(CH$_2$)$_t$" to read -- -A-(CH$_2$)$_r$ --

Column 30, Line 5: Please correct "(ITC)" to read -- (TTC) --

In the Claims

Column 48, Claim 24, Line 53: Please correct "torn" to read -- from --

Signed and Sealed this
Twelfth Day of June, 2018

Andrei Iancu
*Director of the United States Patent and Trademark Office*